United States Patent [19]
Mizuno et al.

[11] Patent Number: 5,417,853
[45] Date of Patent: * May 23, 1995

[54] LIQUID CHROMATOGRAPHIC SYSTEM AND OPERATION METHOD

[75] Inventors: Masako Mizuno, Mito; Kenji Tochigi, Hitachi; Yutaka Misawa, Katsuta, all of Japan

[73] Assignee: Hitachi, Ltd., Tokyo, Japan

[*] Notice: The portion of the term of this patent subsequent to Mar. 15, 2011 has been disclaimed.

[21] Appl. No.: 208,043

[22] Filed: Mar. 9, 1994

Related U.S. Application Data

[63] Continuation of Ser. No. 799,978, Nov. 29, 1991, abandoned.

[30] Foreign Application Priority Data

Nov. 30, 1990 [JP] Japan .................. 2-329019
Feb. 15, 1991 [JP] Japan .................. 3-021789
Mar. 20, 1991 [JP] Japan .................. 3-056840

[51] Int. Cl.$^6$ ............................. B01D 15/08
[52] U.S. Cl. ................... 210/198.2; 210/96.1; 210/143; 210/635; 210/656; 422/70; 436/67; 436/161
[58] Field of Search ............. 210/635, 656, 659, 96.1, 210/101, 143, 198.2; 436/161, 66, 67; 422/70; 530/385, 413, 416, 417

[56] References Cited

U.S. PATENT DOCUMENTS

| | | | |
|---|---|---|---|
| 4,142,856 | 3/1979 | Acuff | 210/656 |
| 4,237,422 | 12/1980 | Lenhardt | 210/656 |
| 4,243,534 | 6/1981 | Bulbenko | 210/656 |
| 4,364,263 | 12/1982 | Sankoorikal | 210/198.2 |
| 4,468,330 | 8/1984 | Kamiyama | 210/656 |
| 4,476,713 | 10/1984 | Alfredson | 210/656 |
| 4,579,663 | 4/1986 | Poile | 210/656 |
| 4,666,713 | 5/1987 | Skelly | 210/656 |
| 4,719,017 | 1/1988 | Uchino | 210/656 |
| 4,732,683 | 3/1988 | Georgiades | 210/656 |
| 4,810,391 | 3/1989 | Bruegger | 210/198.2 |
| 4,840,730 | 6/1989 | Saxena | 210/198.2 |
| 4,861,488 | 8/1989 | Kenny | 210/656 |
| 4,925,567 | 5/1990 | McAleese | 210/656 |
| 4,927,532 | 5/1990 | Pospisil | 210/656 |
| 5,121,443 | 6/1992 | Tomlinson | 210/656 |
| 5,294,336 | 3/1994 | Mizuno | 210/198.2 |

FOREIGN PATENT DOCUMENTS 2126155 5/1990 Japan .................. 210/198.2

OTHER PUBLICATIONS

Binder, Journal of Chromatography, vol. 473, (1989), pp. 325–341.
msr, Berlin 33 (1990), issue 7, pp. 305–308.
Snyder, Introduction to Modern Liquid Chromatography, John Wiley and Sons, Inc., New York, 1979, pp. 489–499 and 542–549.
Patent Office Translation 92-3412 of Japan Patent 2-2126155, Oct. 1992, pp. 1–40.
Rassi, High Performance Liquid Chromatography of Membrane Proteins vol. 3, No. 5 (1988) pp. 188–200.
Kato, High-Performance Liquid Chromatography of Membrane Proteins Journal of Chromatography, 391 (1987) pp. 395–407.
Takahashi, "Measurement of Stable $A_{1C}$ IN $HbA_{1C}$ By HLC-723GHb" JJCLA vol. 12 No. 2 (1987) pp. 133–136.
Patent Office Translation PTO-92-3404 of Takahashi Oct. 1992, pp. 1–14.

Primary Examiner—Ernest G. Therkorn
Attorney, Agent, or Firm—Antonelli, Terry, Stout & Kraus

[57] ABSTRACT

In a liquid chromatographic system for analyzing biological or vital components in blood, etc., a separation column packed with a packing material of organic porous material containing carboxyalkyl groups as functional groups and having pore diameter of 600 to 1,200 Å in dry state and an ion exchange capacity of 0.1 to 0.5 meq/g on dry basis is used to improve the chromatographic performance of the separation column, 5-component and 6-component analysis are carried out by switching separation columns of different column length or diameter, and judgement of column life is made by evaluation parameters.

7 Claims, 11 Drawing Sheets

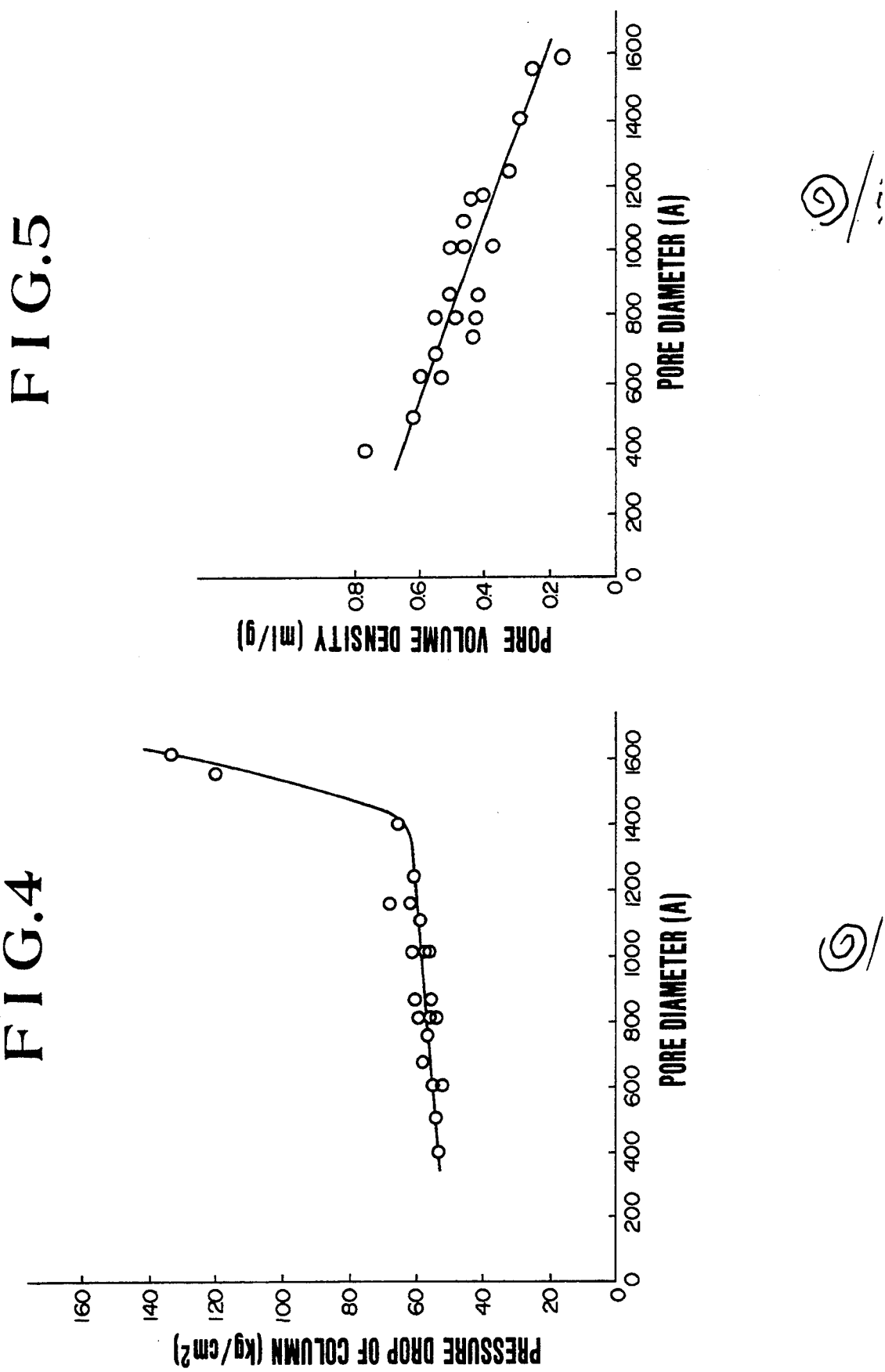

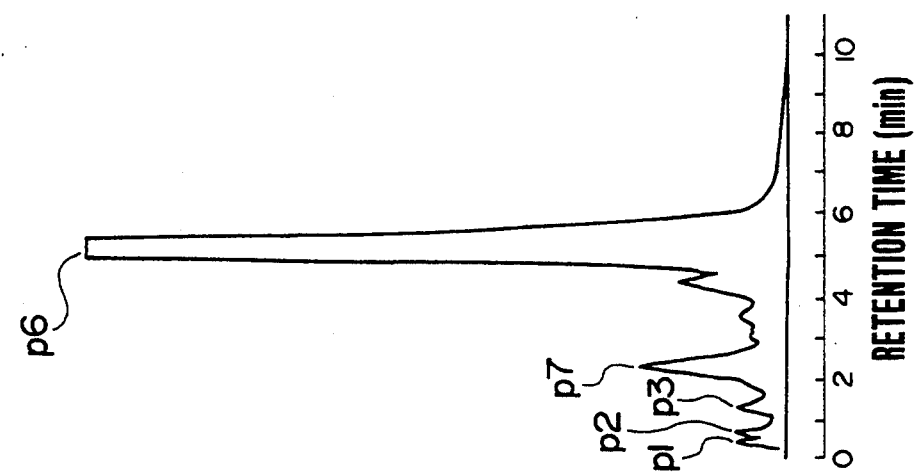
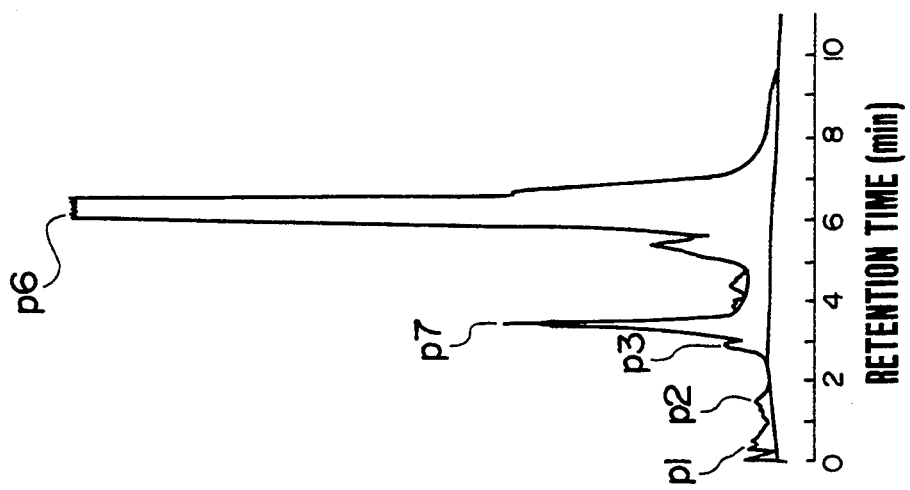
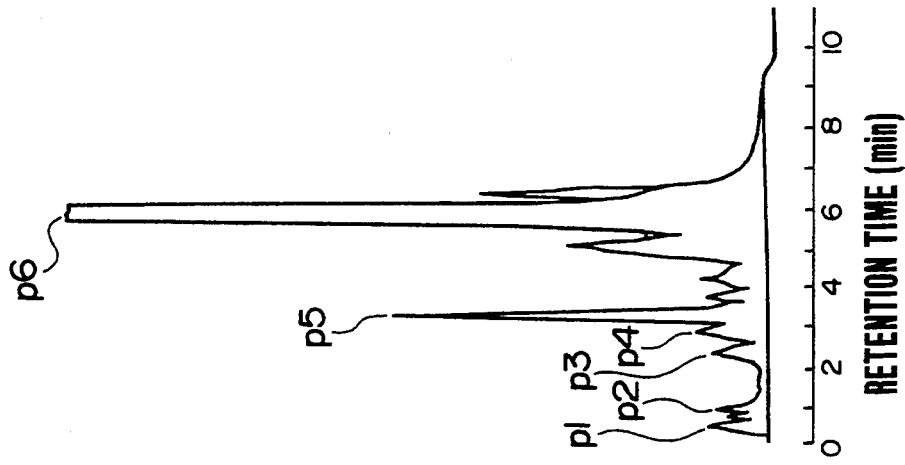

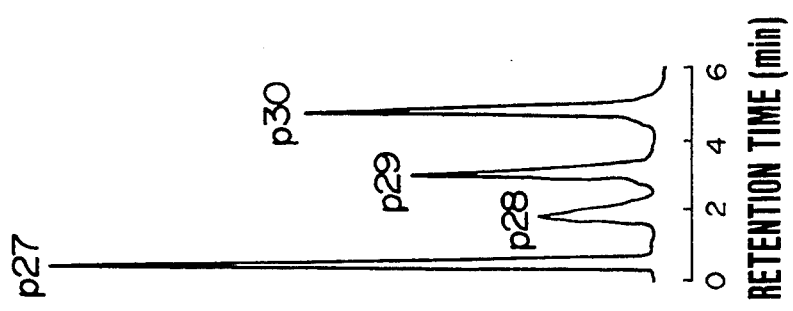
FIG.11
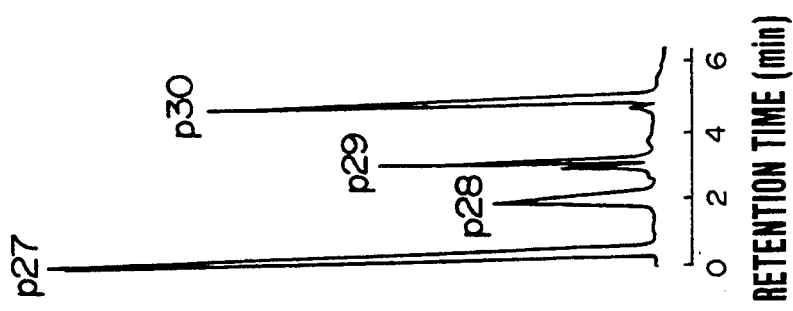
FIG.10
FIG.9

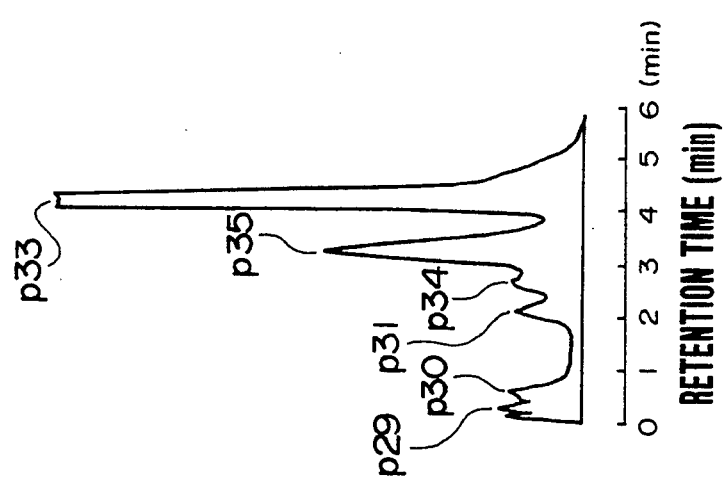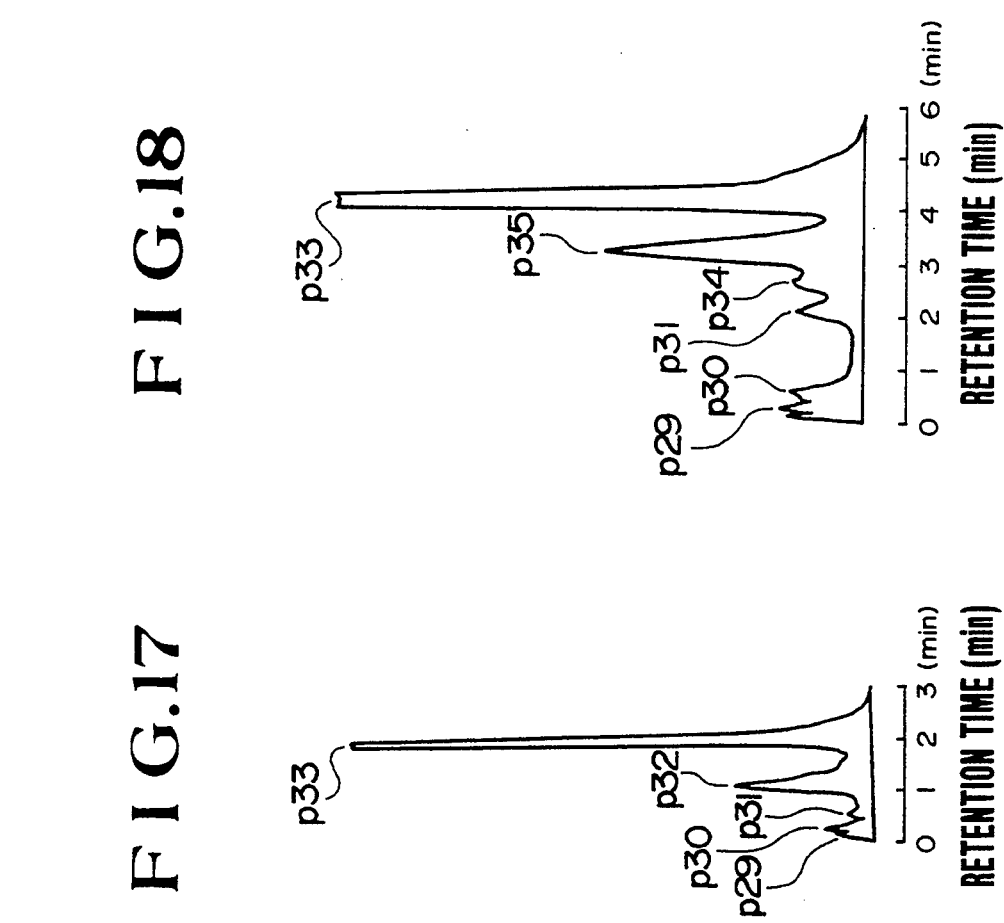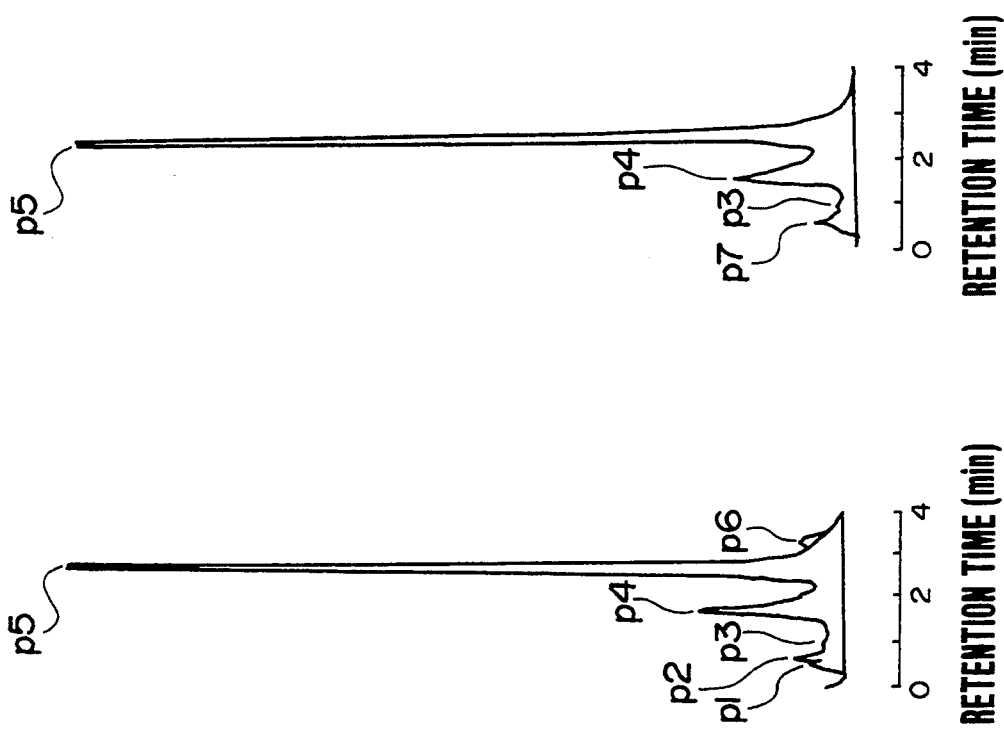

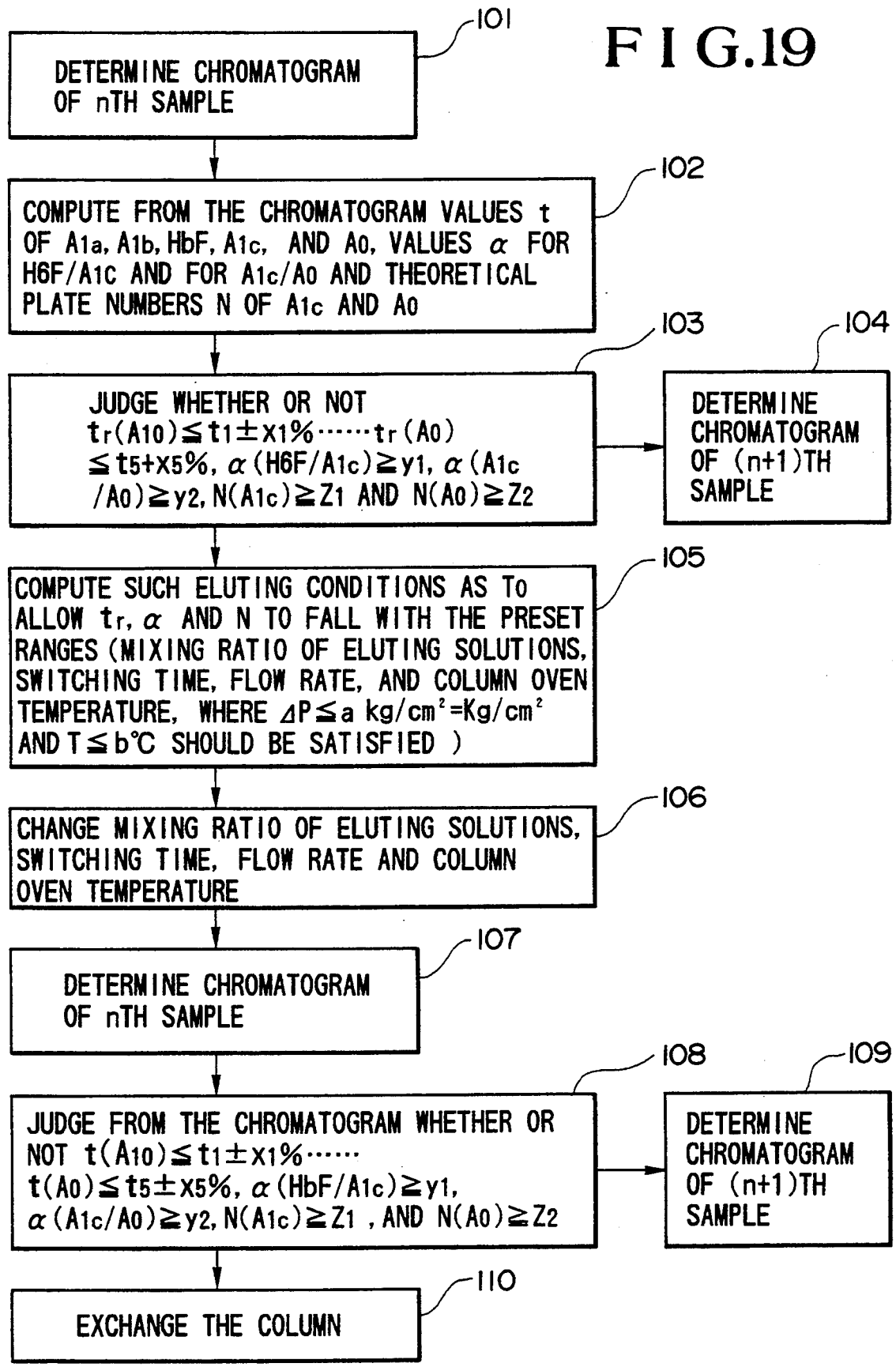

LIQUID CHROMATOGRAPHIC SYSTEM AND OPERATION METHOD

This application is a continuation application of Ser. No. 07/799,978, filed on Nov. 29, 1991, now abandoned.

BACKGROUND OF THE INVENTION

This invention relates to liquid chromatographic system for analyzing biological or vital components, particularly glycated hemoglobins, and their separation column, and packing materials, an eluent, etc. for use in the liquid chromatographic system.

Glycated hemoglobins (GHb) are formed through bonding of sugars in blood to hemoglobins (Hbs) after sugars enters erythrocytes, and it is said that among GHbs, a concentration of $A_{1c}$ refects an average blood glucose concentration past two months.

$A_{1C}$ is non-enzymatically formed through two steps of reaction and is classified into an unstable $A_{1c}$ (l-$A_{1c}$) and a stable $A_{1c}$ (s-$A_{1c}$). Concentration of l-$A_{1c}$ varies by meals or physiological factors and thus it is preferable to determine s-$A_{1c}$, separated from l-$A_{1c}$. It is disclosed by Takahashi et al in Nippon Rinshokensa Jidoka Gakkaishi (Journal of Society of Clinical Inspection Automation of Japan), December issue, page 133 (1987) that in a conventional GHb analyzer it takes 3.5 minutes to separate Hb into 5 components e.g. $A_{1a}$, $A_{1b}$, HbF, $A_{1C}$ and $A_o$ and 8 minutes to separate Hb into 6 components i.e. $A_{1a}$, $A_{1b}$, HbF, l-$A_{1C}$, S-$A_{1C}$ and $A_o$.

In some cases, $A_{1a}$, $A_{1b}$ and HbF are not detected due to low contents thereof on one hand, and Hb or Hb derivatives are contained on the other hand, depending on individual persons, and thus the Hb of every persons is not always separated into the 5 components or the 6 components. Merely for convenience sake, the analysis is herein referred to as 5-component analysis or 6-component analysis.

In the case of separating Hb into 5 components i.e. $A_{1a}$, $A_{1b}$, HbF, $A_{1c}$ and $A_0$ in the foregoing prior art, an eluent of the same composition cannot be used for 6-component analysis, or for separating Hb in to 6 components i.e. $A_{1a}$, $A_{1b}$, HbF, l-$A_{1c}$, s-$A_{1c}$ and $A_0$, depending on the size of a separation column, species of a filler, etc., and thus the eluent must be changed, complicating the operation. Furthermore, such problems as more separation or analysis time required with the so far used conventional packing materials and deterioration of performances of separation column have not been studied yet at all.

SUMMARY OF THE INVENTION

An object of the present invention is to provide a separation column capable of conducting 5-component analysis and 6-component analysis with eluents of the same composition and capable of separating a stable $A_{1c}$, i.e. s-$A_{1c}$ from other Hb components within a short time, and a liquid chromatographic system using such a separation column.

Another object of the present invention is to provide a liquid chromatographic system capable of rationally judging deterioration of performances of a separation column, thereby improving the reliability of analysis, and its operation method.

To attain these objects, the present invention provides a liquid chromatographic system for separating hemoglobin, glycated hemoglobin or hemoglobin derivatives in blood by liquid chromatography which comprises a separation column filled with packing materials of organic porous materials containing functional groups, a means for sampling a sample and transferring the sample and at least one eluent to the separation column, and a means for detecting a concentration of components separated in the separation column, where the packing materials for packing the separation column have pore sizes of 600 to 1,200 Å in a dry state, an ion exchange capacity of 0.1 to 0.5 meq per gram in a dry state, particle sizes of not more than 4 μm and a pore volume density of 0.2 to 0.6 ml/g, and the eluent is a buffer of pH 5.0 to 7.0.

In the present invention, the 5-component analysis and the 6-component analysis can be carried by switching the separation columns.

Still furthermore, a computing means for computing parameters for evaluating the performances of the separation column and an evaluation means for determining whether the computed evaluation parameters are within an allowable range for a present standard values or not, thereby judging deterioration of the performance of the separation column, are provided at the means for determining a chromatogram of component concentrations of the sample from the eluate leaving the separation column.

By selecting the packing material for packing the separation column as above, chromatographic performance can be improved, the separation column can be shortened and the analysis time can be also shortened at the same time in the present invention. Furthermore, by the filling the same packing materials in separation columns of different length, and switching one separation column to another, the 5-component analysis and the 6-component analysis can be carried out with eluents of the same composition.

Still furthermore, the exactness of determination can be improved by provision of the means for evaluating the performance of the separation column, and even in case deterioration of the separation column is judged, the life of the separation column can be extended by changing the conditions of the eluents, etc.

BRIEF DESCRIPTION OF THE DRAWINGS

FIG. 4 is a diagram showing a relationship between the pore size of packing materials and the pressure drop of column.

FIG. 5 is a diagram showing a relationship between the pore size of packing materials and the pore volume density.

FIG. 6 is a chromatogram with packing materials of Sample 1.

FIG. 7 is a chromatogram with packing materials of Comparative Example 1.

FIG. 8 is a chromatogram with packing materials of Comparative Example 2.

FIG. 9 is a diagram showing a relationship between the ion exchange capacity per gram of packing materials (dry basis) and the theoretical plate number.

FIG. 10 is a chromatogram of proteins analyzed with packing materials of the present invention.

FIG. 11 is a chromatogram of proteins analyzed with packing materials of Comparative Example 1.

FIG. 15 is a chromatogram of blood analyzed with the eluents of Sample 7.

FIG. 16 is a chromatogram of blood analyzed with the eluents of Comparative Example 2.

FIG. 17 is a chromatogram in case of 5-component analyzing.

FIG. 18 is a chromatogram in case of 6-component assaying.

FIG. 19 is a flow chart for evaluation processing of performances of separation column.

DESCRIPTION OF THE PREFERRED EMBODIMENTS

Figure 1:
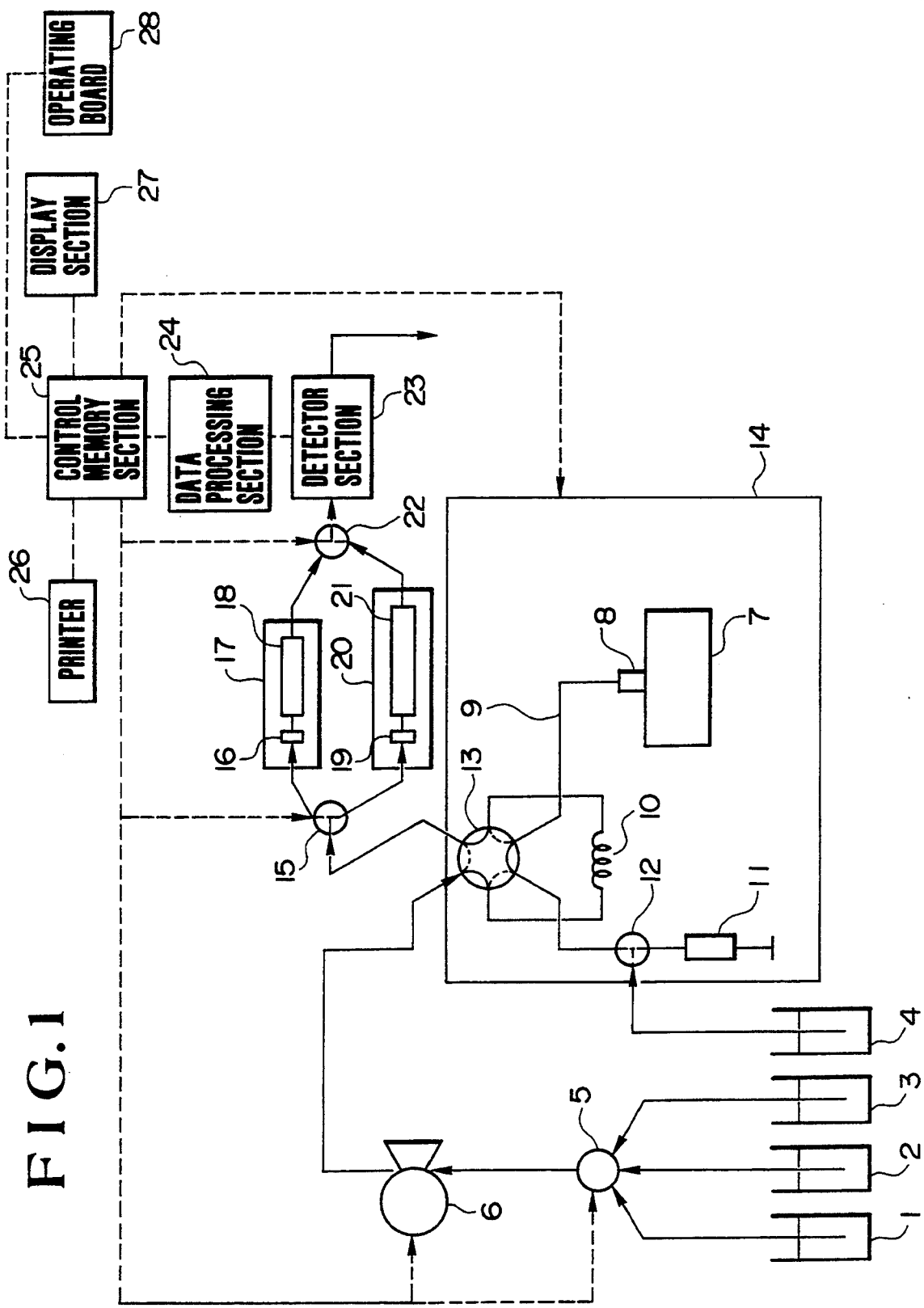
FIG. 1 shows an entire structure of a liquid charomatographic system according to the present invention.

FIG. 1 shows an entire structure of a liquid chromatographic system according to the present invention, where numerals 1 to 3 are eluents, 4 a bottle unit containing a washing solution, 5 is a three-way, electromagnetic valve for selecting any one of the eluents, 6 a feed pump for generating a pressure for transferring the eluting solution 1, 2 or 3 to an autosampler 14, which comprises a sample table 7, a suction nozzle 8, a sample transport pipe 9, a sample loop 10, a six-way valve 13, a cylinder 11 and a three-way valve 12. Furthermore, the eluents and a sample are led to a separation column 18 or 21 through a three-way valve and a prefilter 16 or 19 to extract componets of the sample and then the eluate is led to a detector 23 through a three-way valve. In FIG. 1, a set of two separation columns are used to extract components of the sample in the system, but a single separation column can be used without the three-way valves 15 and 22. Detection signals from the detector 23 is input to a control-memory section (microcomputer) 25 through a data processing section 24 and output to a printer 26 and a display section 27. The control-memory section 25 is also connected to an operating board 28 such as a key board, etc. to set detecting conditions, etc.

In FIG. 1, the data processing section 24 and the control-memory section 25 are provided separately, but can be, of course, integrated into one section without any problem.

The separation columns 18 and 21 and the prefilters 16 and 19 are provided in column thermostats (column ovens) 17 and 20 for adjusting their own temperature, respectively.

Furthermore, the control-memory section 25 is in such a structure as to send control signals to the respective actuators such as the three-way valves, the pump, etc. or receive signals of the actual state from the respective actuators. The control-memory section 25 memorizes evaluation parameters for evaluating the performances of the separation column or data of standard range of the evaluation parameters in a table form. The memorized data can be changed by instructions from the afore-mentioned operating board 28. The signal lines are given as dotted lines in FIG. 1.

Working of the present system will be explained below. A sample set on the sample table 7 is led to the six-way valve 13 through the suction nozzle 8 and the sample transport pipe 9 by a pressure from the cylinder 11, and then is transferred through the three-way valve 15 to the separation column 18 or 21 to be used according to analytical conditions. The sample enters the separation column 18 or 21 through the prefilter 16 or 19. At that time, the amount of the sample is measured through the sample loop 10. Eluents A1, B2 and C3 are passed to the prefilter 16 or 19 through the three-way electromagnetic valve 5, the six-way valve 13 and the three-way valve 15 by the feed pump 6, and then led to the separation column 18 or 21. The eluate from the separation column 18 or 21 is subjected to measurement of light absorbancy at a predetermined wavelength at the detector 23 and the measurements as detection signals are subjected to data processing in the data processing section 24.

A result of assaying by actually changing eluents in the system of FIG. 1 is given below, where a single separation column was used.

In this example, fresh blood containing sodium ethylenediaminetetracetate as an anticoagulant was used as a sample. The blood was diluted with a hemolytic agent (1% Triton X-100 solution) to 200 times by volume and the resulting hemolytic solution was set as a sample onto the sample table 7 in the autosampler 14. The separation column had the following sizes: 4.6 mm in inner diameter and 35 mm long. The column thermostat (column oven) 17 was set to 30° C. In order to remove solid matters from the blood or foreign matters from the eluents, the prefilter 16 was provided before the separation column 18.

The eluent A had the following composition:

33 mM $KH_2PO_4$
7 mM $K_2HPO_4$
pH 6.2

The eluent B had the following composition:

66 mM $KH_2PO_4$
14 mM $K_2HPO_4$
pH 6.2

The eluent C had the following composition:

160 mM $KH_2PO_4$
40 mM $K_2HPO_4$
pH 6.1

Separation of the respective components was carried out by the following stepwise gradient elution:

| Eluent | A: | 0–0.2 min. |
| --- | --- | --- |
| " | B: | 0.3–1.5 min. |
| " | C: | 1.6–1.9 min. |
| " | A: | 2.0–3.5 min. |

Flow rate of the eluents: 1.2 ml/min.

Figure 2:
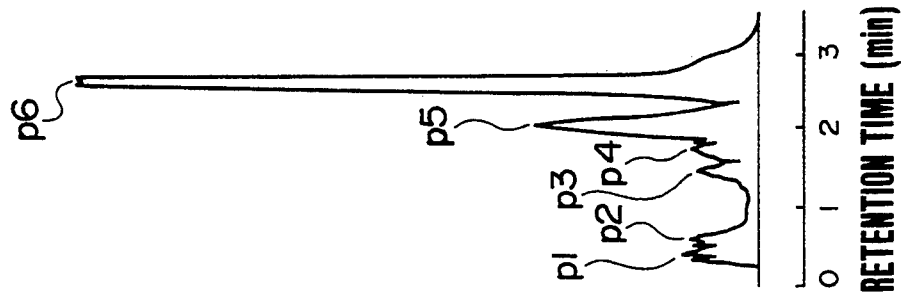
FIG. 2 is a chromatogram of blood analysed by the liquid chromatographic system according to the present invention.

Light absorbancy was measured with a detection wavelength of 415 nm. Chromatogram obtained under the foregoing conditions is shown in FIG. 2, where peak p1 stands for $A_{1a}$, peak p2 for $A_{1b}$, peak p3 for HbF, peak p4 for unstable $A_{1c}$ (l-$A_{1c}$), peak p5 for stable $A_{1c}$ (s-$A_{1c}$), and peak p6 for $HbA_o$. Procedure for identifying the individual peaks will be explained later.

As shown in FIG. 2, hemoglobin in the blood could be separated into 6 componets, i.e. $A_{1a}$, $A_{1b}$, HbF, l-$A_{1c}$, s-$A_{1c}$ and $HbA_o$, within 3.5 minutes. In this manner, the conventional separation time of 8 to 60 minutes required for the separation of s-$A_{1c}$ could be shortened to 3.5 minutes according to the present invention.

A result of investigating packing materials used in the foregoing example will be given below.

Figure 3:
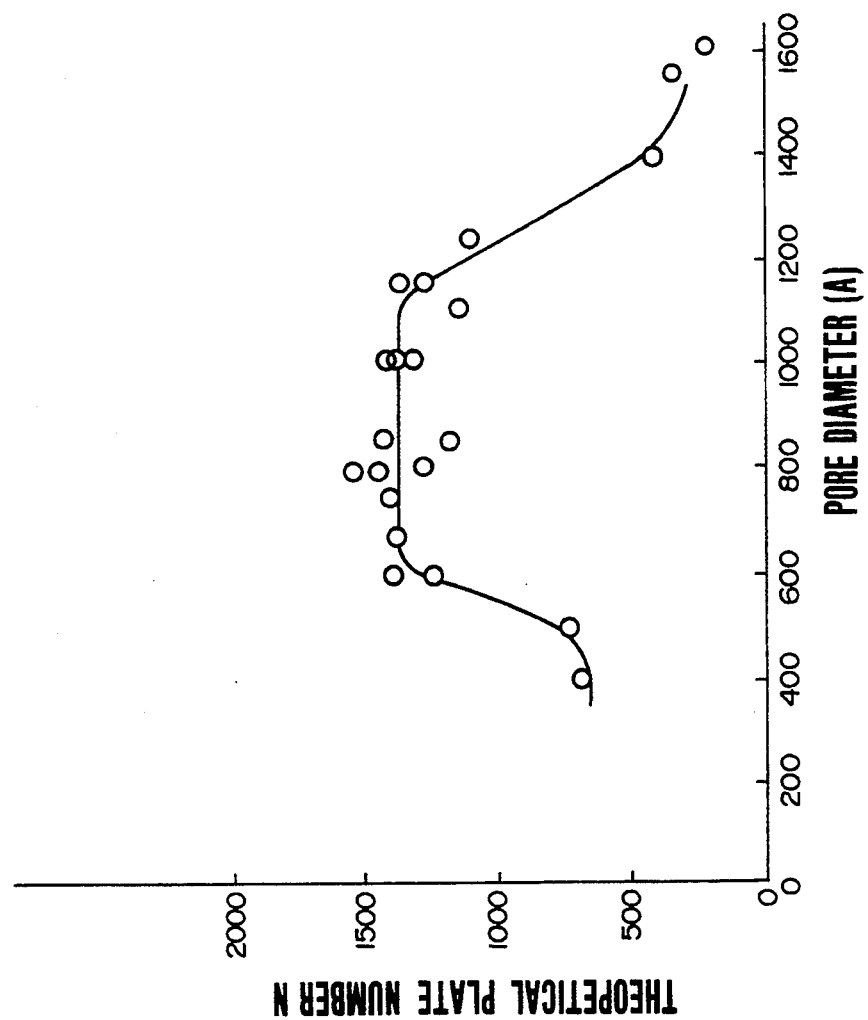
FIG. 3 is a diagram showing a relationship between the pore size of packing materials and the theoretical plate number.

FIG. 3 shows a relationship between the pore diameter of the packing materials and the theoretical plate number N calculated for the peak of $A_{1c}$ (or s-$A_{1c}$), which is a value used as an indicator of peak sharpness in chromatogram and shows that the larger N is, the more sharp a peak is.

FIG. 4 shows a relationship between the pore diameter of the packing materials and the pressure drop $\Delta P$ of the column.

The theoretical plate number N can be obtained according to the following equation (1):

$$N = (tr/\sigma)^2 \quad (1)$$

where tr: retention time of the individual components $\sigma$: standard deviation of peak width The pressure drop $\Delta P$ of the separation column is a difference in pressure between the inlet and the outlet of the separation column, and the larger $\Delta P$ is, the shorter the life of pump seal is. $\Delta P$ also has an influence on the shortening of the life of separation column and can be given by the following equation (2):

$$\Delta P = (\eta L u)/dp^2 \quad (2)$$

$\phi$: permiability coefficient of separation column

L: separation column length u: linear velocity of eluents $\eta$: viscosity of eluents dp: particle diameter of packing materials $\phi$: value dependent on the physical properties of packing conditions of packing materials.

The relationships shown in FIGS. 3 and 4 are those between physical properties of packing materials having an average particle diameter of 3.4 to 3.5 μm after vacuum drying (50° C. for 10 hours), a substantially constant ion exchange capacity of 0.2 to 0.28 meq/gram (dry basis) and pore diameters in a range of 400 to 1,600 Å and chromatographic performances when packed in the column. The packing materials were packed into each column according to a slurry procedure. A 50 mM potassium phosphate solution (pH 6.2) was used as a slurry solvent and a packing solvent. The packing solvent was fed to the individual columns under a packing pressure of 150 kg/cm² for one hour. The columns were stainless steel columns, 4.6 mm in inner diameter and 35 mm long. As a sample, fresh blood of normal human adult, sampled together with sodium ethylenediaminetetracetate as an anticoagulant, was diluted with a hemolytic agent (1% Triton X-100 solution) to 200 times by volume, and used.

As eluents, solutions of potassium dihydrogen phosphate ($KH_2PO_4$) and dipotassium hydrogen phosphate ($K_2HPO_4$) in deionized water at the following concentrations were used:

| Eluent A: | 33 mM $KH_2PO_4$ |
| --- | --- |
| | 7 mM $K_2HPO_4$ |
| | pH 6.2 |
| Eluent B: | 160 mM $KH_2PO_4$ |
| | 40 mM $K_2HPO_4$ |
| | pH 6.1 |

The system shown in FIG. 1 was used without the three-way valves 15 and 22 and the separation column 20. Particularly, Hitachi, type L-6200 intelligent pump was used as the feed pump 6; pump injector having a capacity of 10 μl as the cylinder 11; and Hitachi, type L-2500 data processor as the data processing section 24.

Analysis was carried out at a column temperature of 25° C. with a detection wavelength of 415 nm. Separation of the individual components is carried out according to the following linear gradient elution:

Eluent A/Eluent B = 100/0 by volume for 10 minutes
→Eluent A/eluent solution B = 60/40 by volume Flow rate of eluents: 1.0 ml/min.

Hemoglobin, glycated hemoglobin, etc. in the blood were separated on analyzed with the 21 kinds of the packing materials.

As shown in FIG. 3, the theoretical plate number N was about 1,400 plates in case of using packing materials having pore diameter of 600 Å to 1,200 Å. When the pore diameter was below 600 Å or above 1,200 Å, the theoretical plate number N was decreased and the peak was broadened. Theoretical plate number N was about 700 plates at the pore diameter of 400 Å, and was about 200 plates at the pore diameter of 1,600 Å. Thus, it was found that a pore diameter range of 600 Å to 1,200 Å was suitable for the chromatogarphic performances.

As shown in FIG. 4, the pressure drop $\Delta P$ of the column tends to increase gradually with increasing pore diameters. When the pore diameters exceed 1,400 Å, $\Delta P$ suddenly increases. Packing materials of larger pore diameters have a low mechanical strength, resulting in collapsing or deformation of pores during the packing or measurement and changing in the state of packing, which seems to lead to an increase in $\Delta P$.

As is apparent from FIGS. 3 and 4, a suitable pore diameter of packing materials is 400 Å to 1,400 Å in view of the chromatographic performances and pressure drop of column (permiability of column).

FIG. 5 shows a result of determination of a relationship between the pore diameter and the pore volume density of 21 kinds of the packing materials in a dry state. It can be seen from FIG. 5 that the pore volume density tends to decrease with increasing pore diameter. As is apparent from the foregoing FIGS. 3 and 4 and this FIG. 5 that packing materials having a pore volume density of 0.2 to 0.6 ml/g have a good chromatographic performances and a high permiability.

A result of actual analysis of blood with three kinds of packing materials, i.e. an optimum packing materials, packing materials having a smaller pore diameter and packing materials having a larger pore diameter, found in the foregoing example, will be given below:

Physical properties, etc. of packing materials used are shown in Table 1, where Sample 1 is an optimum packing materials having such a pore diameter as to give good results in the foregoing example, Comparative Example 1 packing materials having a smaller pore diameter and Comparative Example 2 packing materials having a larger pore diameter, and the theoretical plate number N and the pressure drop ΔP were obtained in the same procedure as mentioned before.

TABLE 1

|  | Particle diameter (μm) | Pore diameter (Å) | Pore volume density (ml/g) | Ion exchange capacity (meq/g) | Theoretical plate number N | Pressure drop ΔP (kg/cm$^2$) |
| --- | --- | --- | --- | --- | --- | --- |
| Sample 1 | 3.5 ± 0.4 | 800 | 0.41 | 0.25 | 1500 | 57 |
| Comp. Ex. 1 | 3.5 ± 0.4 | 500 | 0.62 | 0.25 | 730 | 53 |
| Comp Ex. 2 | 3.5 ± 0.4 | 1400 | 0.28 | 0.24 | 420 | 65 |

FIGS. 6, 7 and 8 show chromatograms obtained with the packing materials of Table 1. FIG. 6 shows analytical results with the packing materials of the present invention (Sample 1 of Table 1), where peak p1 stands for $A_{1a}$, peak p2 for $A_{1b}$, peak p3 for HbF, peak p4 for unstable $A_{1c}$ (l-$A_{1c}$), peak p5 for stable $A_{1c}$ (s-$A_{1c}$) and peak p6 for $HbA_0$.

Identification of the individual peaks were carried out in the following procedure.

It is well known that various hemoglobins can be formed by incubating blood and sugar or sugar derivatives, and it is possible to identify the individual peaks by confirming increased peaks.

$A_{1a}$ (peak p1) was confirmed by addition of fructose-1,6-diphosphoric acid (F-1,6-DP), and glucose-6-phosphoric acid (G-6-P), and A1b (peak p2) was confirmed by addition of pyruvic acid. When a chromatogram was determined after addition of glucose to blood, followed by incubation, peak 4 was remarkably increased, and when a chromatogram was determined after incubation in a physiological saline solution, peak p4 was decreased, whereas peak p5 was not changed at all. Thus, it was identified from these facts that peak p4 stood for l-$A_{1c}$ and peak stood for s-$A_{1c}$. Furthermore, peak p4 was identified to stand for HbF from the fact that peak p3 was at the same retention time as that of the main component of umbilical blood.

FIG. 7 shows a chromatogram with packing materials of smaller pore diameter (Comparative Example of Table 1), and FIG. 8 shows a chromatogram with packing materials of larger pore size (Comparative Example 2 of Table 1). In FIGS. 7 and 8, peak p1 stands for $A_{1a}$, peak p2 for $A_{1b}$, peak p3 for HbF, peak p7 for $A_{1c}$, and peak p6 for $HbA_0$. Identification of these individual peaks were carried out in the same manner as that for FIG. 6. In Comparative Examples 1 and 2, it was impossible to separate $A_{1c}$ into l-$A_{1c}$ and s-$A_{1c}$, and the peaks of individual components were broader and the peaks were less sharp than those of Sample 1. The reasons why no satisfactory chromatographic performances was obtained in Comparative Examples 1 and 2 are that the packing materials were not optimized in the pore diameter, pore volume density, etc. and the theoretical plate number N was small. Thus, the packing materials must have a pore diameter of 600 Å to 1,200 Å and a pore volume density of 0.2 to 0.6 ml/g in a dry state.

As explained above, hemoglobin in blood can be separated into further components for the same analysis time in the present invention, and thus more exact determination can be carried out.

Packing materials shown in the following Table 2 was investigated.

TABLE 2

|  | Particle diameter (μm) | Pore diameter (Å) | Pore volume density (ml/g) | Ion exchange capacity (meq/g) | Theoretical plate number N | Pressure drop ΔP (kg/cm$^2$) |
| --- | --- | --- | --- | --- | --- | --- |
| Sample 2 | 3.5 ± 0.4 | 800 | 0.52 | 0.15 | 1180 | 56 |
| Sample 3 | " | 850 | 0.52 | 0.20 | 1300 | 57 |
| Sample 4 | " | 800 | 0.53 | 0.30 | 1300 | 57 |
| Sample 5 | " | 850 | 0.52 | 0.55 | 1200 | 57 |
| Comp. Ex. 3 | " | 800 | 0.55 | 2.0 | 800 | 53 |
| Comp. Ex. 4 | " | 800 | 0.50 | 0.05 | 250 | 54 |

In the investigation, packing materials having a better chromatographic performances (pore diameters of about 800 Å) were selected from the packing materials shown before and their ion exchange capacities were changed to study their influences. The packing materials had methacrylate-based gel as a base material and contained carboxymethyl groups as functional groups, and the packing materials had substantially constant particle diameters, pore diameter and pore volume density, and ion exchange capacities varied in a range of 0.05 to 0.2 meq/g (dry basis). Their chromatograms were determined under the same conditions as before, and their theoretical plate number N and pressure drop ΔP were also measured as shown in Table 2.

A relationship between the ion exchange capacity per gram (dry basis) and the theoretical plate number N is shown in FIG. 9.

In Comparative Example 4 (ion exchange capacity: 0.05 meq/g), the theoretical plate number N was as small as 250 plates, because it seems that the amount of the functional groups (carboxymethyl groups) contained was so small that the exchange reaction between the sample and the packing materials took place not so rapidly. In Comparative Example 3 (ion exchange capacity: 2.0 meq/g), the theoretical plate number N was 800 plates, which was less than those of Samples 2 to 5, and ΔP was by about 10% larger than those of Samples 2 to 5.

Packing materials having a large ion exchange capacity undergo more swelling and shrinkage when the salt concentration of an eluent is changed than packing materials having a small ion exchange capacity. It seems that in case of such packing materials having a large ion exchange capacity the theoretical plate number N was decreased due to the more swelling and shrinkage and unstability or poor permiability. Thus, it is preferable that the ion exchange capacity per gram (dry basis) is 0.1 to 0.5 meq/g.

It can be seen from the foregoing that a esparation column packed with packing materials having a pore diameter of 600 Å to 1,200 Å in a dry state, and an ion exchange capacity of 0.1 to 0.5 meq/g (dry basis) is suitable as a separation column for analyzing hemoglobin, glycated hemoglobin, etc. in blood by liquid chromatography with a high speed and a high separability, particularly as a separation column for chromatographically analyzing stable $A_{1c}$ and unstable $A_{1c}$ for a short time.

Separation of a protein mixture was carried out through separation columns each packed with Sample 1 and Comparative Example 2. The separation columns used had an inner diameter of 4.6 mm and a length of 35 mm each. As a sample, a mixture of standard proteins (mioglobin, ribonuclease, α-chymotrypsinogen A and lysozyme) was used. As eluents, the following solutions D and E each prepared by dissolving potassium dihydrogen phosphate ($KH_2PO_4$) and dipotassium hydrogen phosphate ($K_2HPO_4$) in deionized water to the following concentrations were used.

| Eluent D: | 16.8 mM $KH_2PO_4$ |
| | 8.2 mM $K_2HPO_4$ |
| | pH 7.0 |
| Eluent E: | 16.8 mM $KH_2PO_4$ |
| | 8.2 mM $K_2HPO_4$ |
| | pH 7.0 |

Flow rate of eluent: 1.2 ml/min.
Detection wavelength: 210 nm
Separation of the individual components were carried out according to the following linear gradient elution:
Eluent D/eluent E=100/0 for 4 minutes→From 0% to 100% eluent E for 4 min
The eluent D was passed through the separation column for a period at the time of 4.1 minute up to 6.0 minutes to return the separation column to the initial state.

Chromatograms obtained with the packing material of Sample 1 and that of Comparative Example 2 are shown in FIGS. 10 and 11, respectively, when peak p27 stands for mioglobin, peak p28 for ribonuclease A, peak p29 for α-chymotrypsinogen A, and peak p30 for lysozyme. In FIG. 10, peaks of the individual proteins are sharp, and α-chymotrypsinogen A (peak p29) and lysozyme (peak p30) are clearly separated from peaks which are due to decomposition products and derivatives of proteins or impurities appearing before peaks p29 and p30. In FIG. 11, the retention time of the individual peaks is almost equal to those of FIG. 10, but the peak width is larger than that of FIG. 10. Peaks of α-chymotrypsinogen A and lysozme are not separated from the peaks appearing before the former peaks.

The conventional separation column requires about 30 minutes for the analysis of such a mixture of proteins. In the present invention the physical properties such as pore diameter, ion exchange capacity, etc. are optimized and thus a mixture of proteins can be separated for a shorter analysis time by about 1/5 than the conventional analysis time.

As explained above, a separation column with good chromatographic performances and permiability can be provided according to the present invention, and thus vital components can be effectively separated with a high separability and a high speed.

Effective eluents for analyzing glycated hemoglobin were investigated with packing materials of methacrylate-based gel as a base material containing carboxymethyl groups as functional groups, or packing materials modified with carboxymethyl groups. The packing materials had particle diameters of 3.5±0.4 μm, a specific surface area of 20 $m^2$/g and an ion exchange capacity of 0.28 meq/g. The packing materials were packed in a column, 4.6 mm in diameter and 35 mm long, by a slurry procedure. As a slurry solvent and a filling solvent, a 1M NaCl solution was used and fed to the column under a packing pressure of 150 kg/$cm^2$ for one hour.

As a sample, fresh blood of normal human adult, sampled together with sodium ethylenediaminetetracetate as an anticoagulant, was used after dilution with a commercially available hemolytic agent to 200 times by volume.

The same liquid chromatographic system as in FIG. 1 was used except that a 10 μl injector was used for the injection of a sample in place of the autosampler.

An eluent of the present invention having the following composition was used as Sample 6:

| 46 mM $KH_2PO_4$ |
| 10 mM $K_2HPO_4$ |
| 0.005% (W/V) $NaN_3$ |
| 0.1 mM Triton X-100 |
| pH 6.20 |

Another eluent having the following composition was used as Comparative Example 5 in contrast to the Sample 6.

| 46 mM $KH_2PO_4$ |
| 10 mM $K_2HPO_4$ |
| 0.005% (W/V) $NaN_3$ |
| pH 6.20 |

As shown above, a difference between Sample 6 and Example 5 is in addition of Triton X-100 as a nonionic surfactant to the eluent.

Chromatogram was determined with the foregoing eluents of Sample 6 and Comparative Example 5 by changing the column temperature to 23° C., 30° C., 35° C., 40° C., 45° C., 50° C., 55° C., 60° C., and 65° C., under the following conditions.
Detection wavelength: 415 nm
Flow rate of the eluent: 1.0 ml/min.

Figure 12:
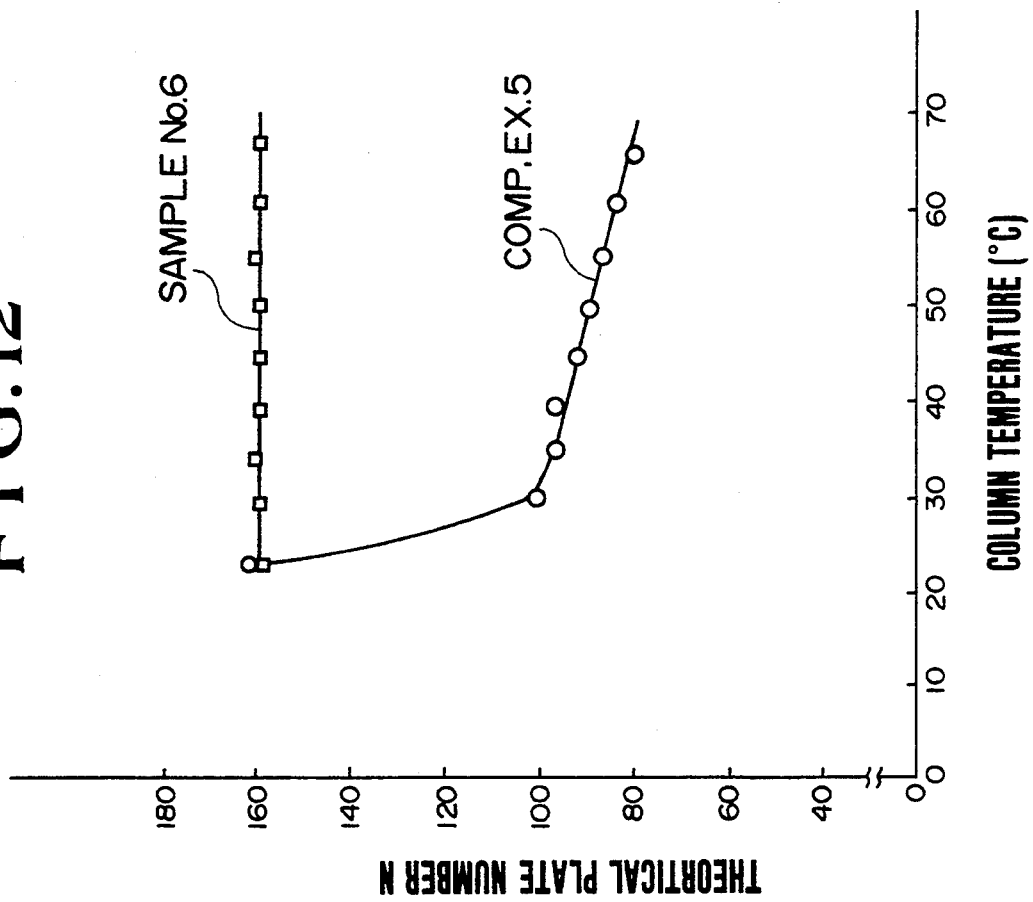
FIG. 12 is a diagram showing a relationship between the column temperature and the theoretical plate number with composition of eluents as a parameter.

FIG. 12 shows a relationship between the column temperature and the theoretical plate number N of component $A_{1c}$ when chromatograms were determined with the eluents of Sample 6 and Comparative Example 5. As is apparent from FIG. 12, the theoretical plate number N was decreased with increasing column temperature in the case of Comparative Example 5, whereas in the case of Sample 6 the value of the theoretical plate number N was almost equal to that at 23° C. even in case the column temperature was increased. The retention $t_r$ of component $A_{1c}$ and pressure drop ΔP of the column were almost same between Sample 6 and Comparative Example 5.

Reasons why the theoretical plate number N was decreased with increasing column temperature seems to be that ionic bonding is dominant as an interaction between the sample and the packing materials, and contribution of other adsorptions than the ionic bonding such as physical adsorption, hydrogen bonding, molecular sieve effect, etc. becomes remarkable with increasing column temperature, resulting in prolongation of the time required for the adsorption and desorption and broadening of peaks.

By adding a non-ionic surfactant such as Triton X-100 to the eluent as in Sample 6, other actions than the ionic bonding such as physical adsorption, etc. can be suppressed without changing the dissociation state of the packing materials, and the broadening of the peaks can be effectively suppressed.

Blood was analyzed with eluents containing Triton X-100 (Sample 6) in the same liquid chromatographic system as shown in FIG. 1. The eluents each had the following composition:

| Eluents a: | 50 mM KH$_2$PO$_4$ |
| | 10 mM K$_2$HPO$_4$ |
| | 0.005% (W/V) NaN$_3$ |
| | 0.1 mM Triton X-100 |
| | pH 6.20 |
| Eluent b: | 62 mM KH$_2$PO$_4$ |
| | 13 mM K$_2$HPO$_4$ |
| | 0.005% (W/V) NaN$_3$ |
| | 0.1 mM Triton X-100 |
| | pH 6.20 |
| Eluent c: | 150 mM KH$_2$PO$_4$ |
| | 50 mM K$_2$HPO$_4$ |
| | 0.005% (W/V) NaN$_3$ |
| | 0.1 mM Triton X-100 |
| | pH 6.10 |

For comparison with Sample 6, chromatograms were also determined with eluents containing no Triton X-100 (a', b' and c': Comparative Example 5). The same liquid chromatographic system as used in FIG. 1 was used.

Column temperature was 23° C., and separation of hemoglobin into the individual components was carried out by the following stepwise gradient elution:

Eluent a or a': 0–0.1 min.
Eluent b or b': 0.2–0.9 min.
Eluent c or c': 1.0–1.4 min.
Eluent a or a': 1.5–4.0 min.

Flow rate of eluent: 1.2 ml/min.

Figures 13, 14:
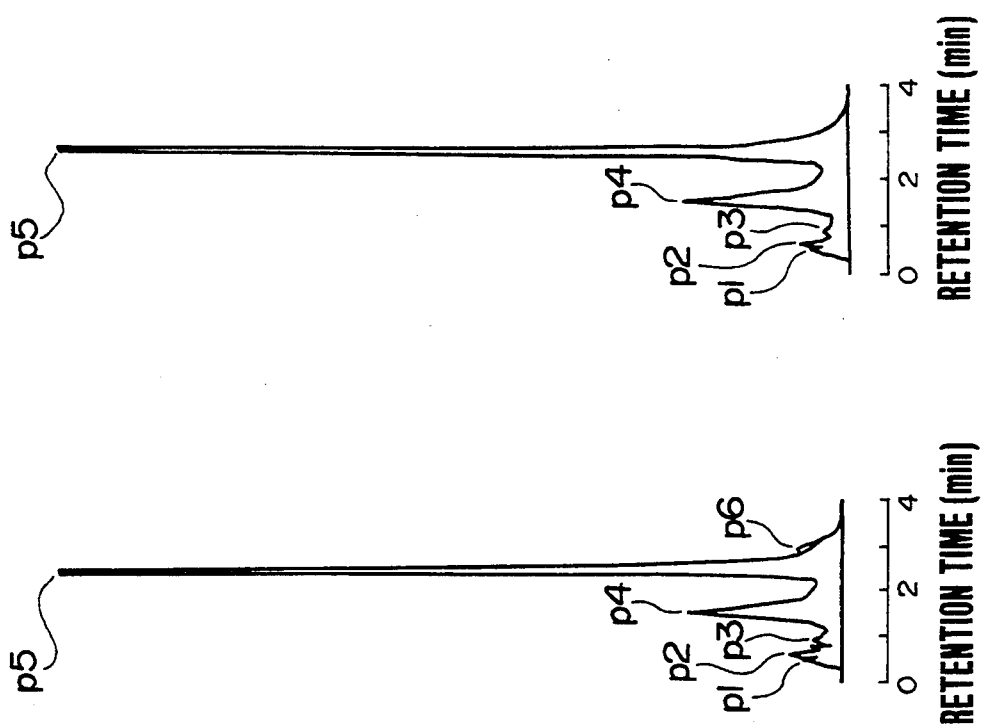
FIG. 13 is a chromatogram of blood analyzed with the eluents of Sample 6.
FIG. 14 is a chromatogram of blood analyzed with the eluents of Comparative Example 1.

FIGS. 13 and 14 show chromatograms obtained with the eluents of Sample 6 and Comparative Example 5 under the foregoing analytical conditions, where peak p1 stands for A$_{1a}$, peak p2 for A$_{1b}$, peak p3 for HbF, peak p4 for A$_{1c}$, and peak p5 for HbA$_o$. In FIG. 14, peak p6 is based on absorption caused by a change in the refractive index due to switching of one eluent to another. The influence on absorption caused by switching of the eluent can be avoided by measuring a reference at a wavelength without any Hb absorption, for example, 690 nm.

As is apparent from FIGS. 13 and 14, the retention time and peak sharpness are almost same between the eluents containing Triton X-100 and the eluents containing no Triton X-100 at the column temperature of 23° C.

That is, no effect of addition of Triton X-100 is obtained at the column temperature of 23° C. as explained before as to Sample 6.

Analysis was further conducted with the same eluents of Sample 6, except that the eluent a of Sample 6 was replaced with an eluent a having the following composition (Sample 7):

Eluent a of Sample 7:

| 42 mM KH$_2$PO$_4$ |
| 9 mM K$_2$HPO$_4$ |
| 0.005% (W/V) NaN$_3$ |
| 0.1 mM Triton X-100 |
| pH 6.20 |

For comparison with Sample 7 as in the case of Sample 6, analyzing was also carried with eluents containing no Triton X-100 (Comparative Example 6).

Separation of hemoglobin into the individual components was carried out by the same stepwise gradient elution as used in Sample 6. Analysis was conducted at a column temperature of 45° C. with a detection wavelength of 415 nm.

FIGS. 15 and 16 show chromatograms obtained by analyzing blood with the eluents of Sample 7 and Comparative Example 6, where peak p1 stands for A$_{1a}$, peak p2 for A$_{1b}$, peak p3 for HbF, peak p4 for A$_{1c}$, peak p5 for HbA$_o$, peak p6 for absorption caused by switching of the eluting solutions, and peak p7 for (A$_{1a}$+A$_{1b}$). In Comparative Example 6 (FIG. 16), the individual peaks are broad, and A$_{1a}$ and A$_{1b}$ are not separated from each other, and also separation of A$_{1c}$ from HbA$_o$ is not satisfactory. In Sample 7 (FIG. 15), good separation was obtained as in the case of 23° C. (FIGS. 13 and 14).

As explained above, good separation can be obtained, even if the separation column is heated, by adding a non-ionic surfactant such as Triton X-100 to the eluent.

Retention time tr of A$_{1c}$ and A$_o$, N' (value similar to the theoretical plate number N, indicating the sharpness of peak) and pressure drop ΔP of column, when glycated hemoglobin was analyzed with eluents of Samples 6 and 7 and Comparative Examples 5 and 6 at column temperatures of 23° and 45° C. are shown in the following Table 3.

TABLE 3

| | Column temperature (°C.) | tr (min) | | N' | | ΔP (kg/cm$^2$) |
| --- | --- | --- | --- | --- | --- | --- |
| | | A$_{1c}$ | A$_o$ | A$_{1c}$ (× 10$^{-3}$) | A$_o$ (× 10$^{-1}$) | |
| Sample 6 | 23 | 1.57 | 2.57 | 4.0 | 4.5 | 62 |
| Comp. Ex. 5 | 23 | 1.53 | 2.52 | 4.0 | 4.4 | 62 |
| Sample 7 | 45 | 1.72 | 2.56 | 3.8 | 4.4 | 47 |
| Comp. Ex. 6 | 45 | 1.68 | 2.52 | 2.8 | 4.0 | 47 |

N' can be obtained according to the following equation (3):

$$N' = (tr \times \text{peak height/peak area})^2 \qquad (3)$$

The equation (3) was derived on the presumption that in the equation (1) σ is proportional to (peak area/peak height). The peak area and the peak height were calculated by type D-2500, data processor.

As apparent from Table 3, N' of component A$_{1c}$ and N' of component Ao in the case of using eluents each containing Triton X-100 at 45° C. (sample 7) are the same as N's at 23° C. (Sample 6 and Comparative Example 5). ΔP is lower at the higher column temperature, whereas ΔP of Sample 7 is by about 75% lower than those of Sample 6 and Comparative Example 5.

As explained above, a chromatogram showing the same separability as at room temperature can be obtained, even if the separation column is heated, by adding a non-ionic surfactant to eluents. Pressure drop ΔP of the separation column is lower when the analysis is carried out in a heated column than at room temperature, and an influence on a pump seal is less. Since the pressure on the column is lower, an effect on the prolongation of column life can be also obtained. Furthermore, the flow rate of eluent can be increased in the case of a heated column, as compared with the room temperature, and thus higher assaying speed can be obtained.

As explained above, the running cost of a liquid chromatographic system can be reduced by optimizing eluent, thereby controlling the operating temperature as in the present invention, and analytical results of good reproducibility can be obtained on account of less dependency on the column temperature. That is, diagnosis and treatment of diabetes can be more exactly carried out.

A liquid chromatographic system for analyzing with two separation columns as shown in FIG. 1 will be explained below. The entire structure of the system has been already explained before, and thus will be omitted. Only the specification of the separation columns, compositions of eluents, procedure for preparing a sample to be used will be given below.

As a packing material for analyzing GHb, a packing material of methacrylate-based gel as a base material containing carboxymethyl groups as functional groups, which had a particle diameter of 3.5±0.7 μm, an ion exchange capacity of 0.28 meq/g (dry basis), a pore diameter of 700 Å and a specific surface area of 15 m$^2$/g, was used. For the measurement of physical properties of the packing material, the packing material was dried at 70° C. under the atmospheric pressure and then vacuum dried at 50° C. for 10 hours.

Two kinds of stainless steel columns, i.e. 4.6 mm in inner diameter and 35 mm long (for analyzing 5 components) and 4.6 mm in inner diameter and 80 mm long, (for analizing 6 components were used. The packing material was packed into the columns by a slurry procedure, where a 50 mM phosphate buffer solution was used as a slurry solvent and a packing solvent. The packing solvent was fed to the 35-mm long column under a packing pressure of 150 kg/cm$^2$ and to the 80-mm long column under a packing pressure of 200 kg/cm$^2$, each for one hour.

As a sample, fresh blood, sampled together with sodium ethylenediaminetetracetate as an anticoagulant, was used after dilution to 200 times by volume with a hemolytic agent (a 0.1% Triton X-100 solution), and set onto the sample table 7 of autosampler, as shown in FIG. 1.

As separation columns, the stainless steel columns, i.e. 4.6 mm in inner diameter and 35 mm long and 4.6 mm in inner diameter and 80 mm long, packed with the packing material of methacrylate-based gel containing carboxymethyl groups and having an average particle diameter of 3.5 μm were used (18 and 21 in FIG. 1).

As eluents, eluents A, B and C with the following composition were used:

| | |
|---|---|
| Eluent A: | 42 mM KH$_2$PO$_4$ |
| | 9 mM K$_2$HPO$_4$ |
| Eluent B: | 62 mM KH$_2$PO$_4$ |
| | 13 mM K$_2$HPO$_4$ |
| Eluent C: | 150 mM KH$_2$PO$_4$ |
| | 50 mM K$_2$HPO$_4$ |

Eluting conditions (switching time for eluent, flow rate, column temperature, etc.) for 5-component analysis (separation of Hb into $A_{1a}$, $A_{1b}$, HbF, $A_{1c}$ and Ao) and 6-component analysis (separation of Hb into $A_{1a}$, $A_{1b}$, HbF, l-$A_{1c}$, s-$A_{1c}$ and Ao) are given below.

Separation of Hb into the individual components in the 5-component analysis was carried out by the following stepwise gradient elution:
Eluent A: 0–0.4 min.
Eluent B: 0.5–1.4 min.
Eluent C: 1.5–1.8 min.
Eluent A: 1.9–3.0 min.
Flow rate of eluent: 1.4 ml/min.
Columu temperature: 40° C.

In the case of 6-componet analysis, the following stepwise gradient elution was employed:
Eluent A: 0–0.1 min.
Eluent B: 0.2–2.5 min.
Eluent C: 2.6–3.4 min.
Eluent A: 3.5–6.0 min.
Flow rate of eluent: 1.0 ml/min.
Column temperature: 40° C.

Working of the individual members of the system shown in FIG. 1 will be explained, at first, in the case of 5-component analysis.

A sample set onto the sample table 7 is led to the sample loop 10 through the suction nozzle 8, the sample transport pipe 9 and the six-way valve 13 by the syringe 11. In the sample loop 10 (capacity: 10 μl), the amount of the sample is measured. Then, the six-way valve 13 is switched. Washing solution 4 is led to the six-way valve 13, the sample loop 10, etc. through the three-way valve 12 to wash the pipings.

Eluents 1, 2 and 3 (A, B and C) are stepwise led to the separation column 18 (4.6 mm in inner diameter and 35 mm long) according to the gradient conditions through the three-way valve 15, the six-way valve 13, the sample loop 10 and the prefilter 16 by the feed pump (intelligent pump) 6. The column thermostat (oven) 17 is set to 40° C. As the eluents are led to the separation column 15, the sample in the sample loop 10 is fed to the separation column 18. In the separation column 18, Hb is separated into individual components. Light absorbancy of the eluate from the separation column 18 is measured by the UV-VIS detector 23 [measuring wavelengths: 415 nm and 690 nm (reference)]. The resulting chromatogram is shown in FIG. 17, where peak p29 stands for $A_{1a}$, peak p30 for $A_{1b}$, peak p31 for HbF, peak p32 for $A_{1c}$, and peak p33 for $A_0$. Under this condition, Hb can be separated into 5 components, i.e. $A_{1a}$, $A_{1b}$, HbF, $A_{1c}$ and $A_0$ in a cycle of 3.0 min, as shown in FIG. 17. From the chromatogram, a ratio of component $A_{1c}$ to total Hb components is obtained by the data processor 24.

In the case of 6-component analysis, a separation column 21 (4.6 mm in inner diameter and 80 mm long), a prefilter 19 and a column thermostat 20 are used. The flow of sample and the eluents is the same as that in the case of the 5-compoent analysis. A plurality of separation columns may be provided in one thermostat.

Analysis is carried out in the separation column 18 under the afore-mentioned gradient conditions. A chromatogram thus obtained is shown in FIG. 18, where peak p29 stands for $A_{1a}$, peak p30 for $A_{1b}$, peak p31 for HbF, peak p34 for l-$A_{1c}$, peak p35 for s-$A_{1c}$ and peak p33 for $A_0$. Separation of Hb into 6 components, i.e. $A_{1a}$, $A_{1b}$, HbF, l-$A_{1c}$, s-$A_{1c}$ and $A_0$ can be carried out in a cycle of 6.0 minutes, as shown in FIG. 18. A ratio of s-$A_{1c}$ to total Hb components is obtained by the data processor 24.

Once programs of a plurality of eluents are input in advance, different types of analysis can be continuously carried out without exchange of column or eluents but only by selecting a desired program by the operating board 28 such as a switch or key. For example, when 6-component analysis is to be carried out after 5-component analysis, such instructions are input in advance by a key board. Then, the control-memory section 25 send a signal to the feed pump 6, the three-way valve 15, and the column thermostats (ovens) 17 and 18 on the basis of the output from the data processor 24 to change measuring conditions for column to be used, mixing ratio and flow rate of eluents, column temperature, etc. Furthermore, instructions on which sample is to be analyzed are sent to the autosampler 14. In this manner, the 5-component analysis and the 6-component analysis can be continuously carried out.

After a run of 5-component analysis has been conducted on samples set onto the sample table of autosampler 14, 6-component analysis of only samples whose $A_{1c}$ valve has exceeded the standard value can be carried out. Percentage of component $A_{1c}$ is computed by the data processor 24 and the computed percentage is judged in the control-memory section 25 on whether it exceeds the standard value or not. From the control-memory section 25, signal of sample number that exceeds the standard value is sent to the autosampler 14 and only such a sample is subjected to the 6-component analysis. Furthermore, from the control-memory section 25, the signal is sent to the feed pump 6, the three-way valve 15, column thermostats (ovens) 17 and 18, etc. to change the measuring conditions to those for the 6-component analysis.

As already explained before, $A_{1c}$ consists of l-$A_{1c}$ and s-$A_{1c}$, and s-$A_{1c}$ has a correlation to the blood glucose concentration past two months. l-$A_{1c}$ depends on meals, etc. and thus it is desirable to determine s-$A_{1c}$. However, determination of s-$A_{1c}$ by 6-compoent analysis requires double analysis time, as compared with the determination of $A_{1c}$ (that is, the analysis time for determination requires 3 minutes, whereas that for s-$A_{1c}$ determination 6 minutes). Thus, the $A_{1c}$ determination is carried out for all the samples, and the s-$A_{1c}$ determination is carried out for only samples whose value exceeds the standard value, whereby total analysis time can be shortened.

As explained above, the present liquid chromatographic system can perform analysis of two or more different types with the same eluents only by changing separation column or column temperature and gradient program (mixing ratio of eluents, switching time, flow rate of eluents, etc.). Since analysis of different types can be carried out without changing the eluents as above, there is no such troublesome time of exchanging the eluents and also the running cost can be decreased. Furthermore, analysis of different types can be carried out continuously and thus the analysis time can be shortened.

Thus, the present invention can provide a liquid chromatography system capable of automatically analyzing different fractions.

A method for prolonging the life of separation column and carrying out analysis with high exactness by detecting deterioration of performance of a separation column and changing eluting conditions, for example, compositions and flow rate of eluents, switching time, column temperature, etc. will be explained below.

The present invention has been also established on the basis of such a finding that, so long as a sample can be correctly separated in a liquid chromatographic system, such parameters as retention time, selection coefficient, theoretical plate number, etc. of specific components obtained from the chromatogram fall within given ranges and also such a finding that, even if a separation column reaches its life under a set of predetermined eluting conditions, much more samples can be still analyzed by improving the parameters that can change the eluting conditions. Thus, the present invention is to prevent lowering of exactness in analyzing by using these parameters as evaluation values for judging the presence or absence of performance of a separation column and informing users of column deterioration earlier while changing the eluting conditions on the basis of the evaluation results and attempting to prolong the life of the separation column.

As the evaluation parameters, at least one of retention time, capacity factor, selection coefficient, full width or half width of peaks corresponding to the individual components, standard deviations $\sigma$ of the individual peaks or variance $\sigma^2$, ratio of weak width to peak height, asymmetric factor of the individual peaks, theoretical plate number, and linearity of base line must be used. Furthermore, it is preferable to set the evaluation parameters in accordance with predetermined specific components of samples.

Relationships between the separability and various evaluation parameters relating to the performance evaluation of a separation column will be explained below:

In liquid chromatography, resolution Rs is given according to the following equation (4):

$$Rs = (1/4) \cdot (\alpha - 1) \cdot (K'/(K' + 1)) \cdot \sqrt{N} \qquad (4)$$

N, K' and $\alpha$ can be obtained from a chromatogram according to the following equations (5), (6) and (7):

$$N = (tr/\sigma)^2 \qquad (5)$$

$$K' = (tr - to)/to \qquad (6)$$

$$\alpha = K'_2/K'_1 = (tr_2 - to)/(tr_1 - to) \qquad (7)$$

wherein tr, $tr_1$ and $tr_2$ each are retention time (where $tr_1 < tr_2$), to is retention time of a component having no interaction with a packing material and $\sigma$ is a standard deviation.

When the column length is constant, $\alpha$ or K' (or tr) depends on the packing material, compositions of the eluents, column temperature T and flow rate F (or linear velocity u) of the eluents.

In liquid chromatography, pressure drop $\Delta P$ of the column is a factor that determines the eluting conditions, as explained before. $\Delta P$ is obtained according to the equation (2) as already mentioned and given below:

$$\Delta P = \phi(\eta L U)/d_p^2 \qquad (2)$$

When the same separation column is used, $\phi$, L and $d_p$ can be presumed to be constant in the equation (2), because the packing material and the column length are constant. Thus, $\Delta P$ depends on the viscosity $\eta$ of eluents and the linear velocity u of the eluents (u is proportional to the flow rate F, when the column diameter is constant). The viscosity $\eta$ is influenced by a column temperature.

When $\Delta P$ exceeds some value (critical pressure), a sudden increase in $\Delta P$ is observable due to deformation of the packing material or a change in the packing state, and thus it is necessary to set eluting conditions (column temperature T and flow rate F of eluents) so that $\Delta P$ may be lower than the critical pressure.

Relationships between measuring conditions, i.e. compositions of eluents, flow rate F of eluents, column temperature T, etc. and such values as theoretical plate number N, retention time tr, selection coefficient $\alpha$, pressure drop $\Delta P$, etc., and ranges for N, tr, $\alpha$, $\Delta P$, etc., capable of conducting preferable separation of samples must be obtained in advance by calculation or tests, and N, tr, $\alpha$ and $\Delta P$ are calculated from chromatograms. When it is found that these values are outside the ranges capable of conducting preferable separation, appropriate compositions of eluents, F, T, etc. can be obtained from the relationships between the measuring conditions, i.e. the compositions of eluents, F, T, etc. and such values as N, Tr, $\alpha$ and $\Delta P$.

Besides the above-mentioned evaluation parameters, it is possible to use a capacity factor, full width or half width of peaks each corresponding to the individual components, standard deviations $\sigma$ of the peaks, or their variance $\sigma^2$, ratio of peak width to peak height, asymmetrical factors of the peaks, linearity of base line, etc. as evaluation parameters. Besides the above-mentioned eluting conditions, a mixing ratio, species and flow rate of eluents, switching time of species of passing eluents, etc. can be included in the eluting conditions.

By providing the computing section in a liquid chromatographic system and changing measuring conditions such as compositions and flow rate of eluents, column temperature, etc. according to signals from the computing section, much more samples can be analyzed with the same separation column as the conventional one.

Working of the present invention will be explained below, referring to drawings. The foregoing treatments are carried out in the data processing section 24 and the control-memory section 25 as shown in FIG. 1. FIG. 19 shows a flow chart of the treatments and performance evaluation.

The data processing section 24 receives measurement data of chromatogram of nth sample measured by the detection section 23 (Step 101). Then, evaluation parameters of predetermined specific items are determined on the basis of the received measurement data in the data processing section 24 (Step 102). That is, the retention time tr each of $A_{1a}$, $A_{1b}$, HbF, $A_{1c}$ and $A_0$ componets, selection coefficient $\alpha$ for HbF and $A_{1c}$, selection coefficient $\alpha$ for $A_{1c}$ and $A_0$ and theoretical plate numbers N for $A_{1c}$ and $A_0$ components are calculated therein. Besides tr, $\alpha$ and N, peak width, standard deviations $\sigma$, variances $\sigma^2$, capacity factors K', etc. of specific components can be used as indicators for the performance evaluation of the separation column. For example, retention time tr each of the individual components and theoretical plate number N of component $A_{1c}$ are computed in Examples of FIGS. 20 and 21 which follows, respectively.

The control-memory section 25 judges whether the thus obtained evaluation parameters fall within specific allowable ranges of predetermined standard values or not (Step 103). Allowable range of tr, $\alpha$, N, etc. that permit good separation are to be preset. In Step 103 of FIG. 19, $t_1$ to $t_5$ are standard values of retention time tr and $X_1$ to $X_5$ are preset allowable ranges, and whether the thus obtained values of tr and N fall within the preset ranges that permit good separation or not is judged, for example, whether values of tr of the individual components fall within $\pm 10\%$ and N is more than 500 plates or not is judged. As a result of the judgements, a signal is sent to the autosampler 14 from the control-memory section 25, when the values of tr and N fall within the preset allowable ranges, to conduct analysis of n+1th sample (Step 104).

On the other hand, when it is found as the result of the judgements that at least one of the thus obtained evaluation parameters falls outside the preset allowable ranges, change factors and values for the eluting conditions are to be obtained in accordance with correlations between the eluting conditions and the evaluation parameters memorized in the data table in advance to make the deviated evaluation parameter fall with the allowable ranges (Step 105). For example, when at least one of values of tr and N does not fall within the preset allowable ranges, computation is to be conducted in the control-memory section 25 on the basis of the values of tr or N obtained from chromatograms and correlation data between the concentration (mixing ratio of solution A to solution B) of eluents (first solutions) and values of tr or N (FIGS. 20 and 21) to obtain such measuring conditions as to allow values of tr to fall within $\pm 10\%$ of the initial values or N to take more than 500 plates. When such measuring conditions as to allow values of tr to fall within $\pm 10\%$ of the initial values or N to take more than 500 plates was computed on the basis of the values of tr or N obtained from the chromatogram of 1,300th sample and the correlations of FIG. 20 or 21 in that case, it was found that good separation could be obtained by setting a ratio of solution A to solution B to 65/35 as the first solutions.

Then, the memory-control section 25 controls change of eluting conditions such as a mixing ratio of eluents, switch time, flow rate, column oven temperature, etc. on the basis of the results of computation (Step 106). That is, signals are sent to the three-way electromagnetic valve 5, the feed pump 6 and the column oven 17 or 20 of FIG. 1 to change the mixing ratio of eluents, switch time, flow rate and column oven temperature. For example, a signal is sent to the three-way electromagnetic valve 5 to change the mixing ratio of eluents (first solutions) from a ratio of solution A/solution B=60/40 (initial measuring conditions) to a ratio of solution A to solution B=65/35.

In order to conduct confirmation and correct analysis, a signal is sent to the autosampler 14 from the computing section 25 to sample an nth sample (1,300th sample) once again to determine a chromatogram (Step 107).

Then, the same treatments as in Steps 102 and 103) are carried out on the basis of the chromatogram obtained in Step 107 (Step 108), and when the results are found to be satisfactory, step 109 is carried out to analyze next n+1th sample. When the results are found to be unsatisfactory, step 110 is carried out to output such instructions as to change the separation column or such information that the performance is deteriorated, or the like on the printer 26 or display section 27 (Step 110).

Before analyzing nth sample in Step 107, it is possible to determine a chromatogram with a commercially available standard sample to check the column performance.

General tendency of correlations between the evaluation parameters as indicators of column performance and the eluting conditions will be explained below. Among the evaluation parameters, the retention time tr mainly depends on the composition of eluents (mixing ratio), column temperature, flow rate of the eluents, and switching time of eluents. The selection coefficient e depends on the composition of eluents (species, mixing ratio, etc.) and switching time of eluents. Values as indicators of sharpness of peaks, such as theoretical plate number N, peak width (half width and standard deviation a of peaks), etc. depend on the column temperature and flow rate of eluents. When the values of evaluation parameters fall outside the preset allowable ranges on the correlations between the eluting conditions and evaluation parameters as indicators of column performance memorized in advance, eluting conditions such as composition (species, mixing ratio, etc.) of eluents, column temperature, flow rate of eluents, switching time of eluents, etc. are changed.

When there is a difference in the priority in correlations between the eluting conditions and the evaluation parameters, eluting conditions to be changed according to the difference in the priority in correlations are selected. For example, when the value of tr falls outside the preset allowable range, eluting conditions must be changed in the order of priority, i.e. order of (1) composition of eluents (mixing ratio), (2) flow rate and switching time of eluents, and (3) column temperature. When the value of α deviates from the present allowable range, change must be made in the order of (1) composition of eluents (mixing ratio) and (2) switching time of eluents. When values of theoretical plate number N, peak width, etc. fall outside the preset allowable range, change must be made in the order of (1) compositions of eluents (mixing ratio), (2) flow rate of eluents and (3) column temperature. By changing the eluting conditions in these orders, it is possible to set eluting conditions efficiently.

In case of analyzing glycated hemoglobin, the proteins in blood will be denatured with increasing column temperature, and thus it is preferable that the column temperature is not higher than 55° C. Furthermore, measuring conditions must be set so that the pressure drop of the column may be below the critical pressure. That is, eluting conditions must be set in view of the heat stability of samples, pressure resistance of the column, etc.

Results of actual experiments will be given below:

The same system as in FIG. 1 without the three-way valves 15 and 22 and with a single separation column i.e. separation column 18 was used. Fresh blood sampled together with sodium ethylenediamine tetracetate as an anticoagulant was used as a sample. After dilution of the blood sample with a commercially available hemolytic agent to 200 times by volume, the sample was set onto the sample table 7 of autosampler 14 of FIG. 1. Stainless steel column (4.6 mm in inner diameter, 35 mm long) filled with a weakly acidic, cation exchange resin of methacrylate-based gel as a base material containing carboxymethyl groups as functional groups, having particle diameter of 4.1 μm as a packing material was used as separation column 18. Prefilter 16 was provided before the separation column 18 to prevent solid matters (memblanes, etc.) in blood or impurities in the eluents from entering into the separation column 18 and from the resulting increase in the pressure drop of the column or deterioration of the packing materials. Temperature of column oven 17 for controlling the temperature of separation column 18 was initially set to 25°. The following eluents A, B and C, each containing potassium dihydrogen phosphate ($KH_2PO_4$) and dipotassium hydrogen phosphate ($K_2HPO_4$) dissolved in deionized water at the following concentrations, respectively, were used.

| Eluent A: | 33 mM $KH_2PO_4$ |
| | 7 mM $K_2HPO_4$ |
| | pH 6.2 |
| Eluent B: | 66 mM $KH_2PO_4$ |
| | 14 mM $K_2HPO_4$ |
| | pH 6.2 |
| Eluent C: | 160 mM $KH_2PO_4$ |
| | 40 mM $K_2HPO_4$ |
| | pH 6.1 |

Separation of the individual components were carried out according to the following stepwise gradient elution, where a ratio of solution A/solution B in the first solution was by volume:

First solution (eluent): solution A/solution B=60/40: 0–0.2 min.

Second solution (eluent): solution B: 0.3–1.5 min.

Third solution (eluent): solution C: 2.0–1.9 min.

First solution (eluent): solution A/solution B=60/40: 2.0–3.5 min.

Flow rate of eluent: 1.0 ml/min.

The sample set onto the sample table 7 was led to the six-way valve 13 through the suction nozzle 8 and the sample transport pipe 16 by the cylinder 11, and then led to the separation column 18 through the prefilter 16. The amount of the sample to be led to the separation column 18 was measured through the sample loop 10. In the experiments, 10 μl of a sample was measured by the sample loop 10. Washing solution 4 was introduced into the system through the three-way valve 12 to wash the six-way valve 13 and the piping in the sample loop 10. Eluents A, B and C were led to the separation column 18 through the three-way electromagnetic valve 5 by the feed pump 6 (intelligent pump). Eluate from the separation column 18 was led to the detector 23 to measure light absorbancy with wavelength of 415 nm and that of 690 nm (reference). The measurement with the wavelength of 690 nm was to correct the light absorbancy due to the switching of the eluents.

Figure 22:
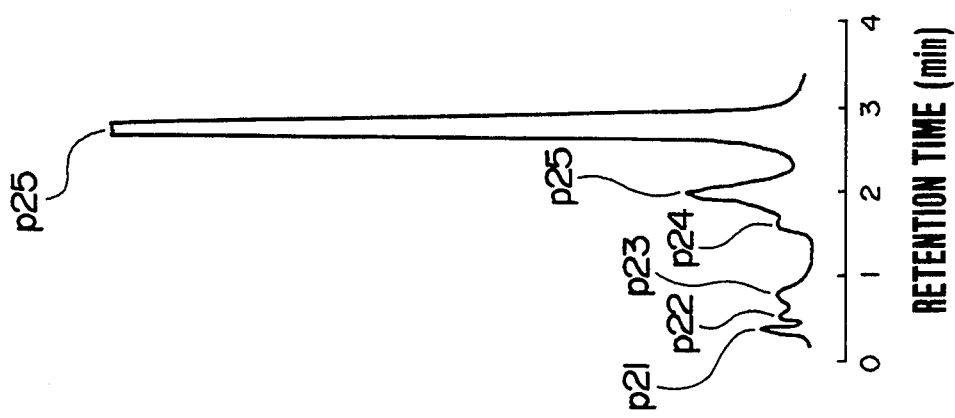
FIG. 22 is a chromatogram of analyzing when the separation column is fresh.
Figure 23:
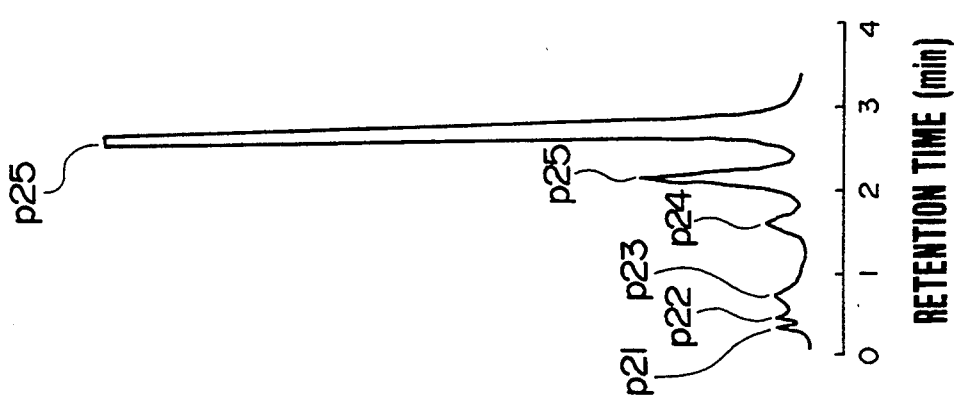
FIG. 23 is a chromatogram of analyzing when the separation column is old.

Among chromatograms determined under these measuring conditions, a chromatogram of 10th sample is shown in FIG. 22 and that of 1,300th sample is shown in FIG. 23. As is apparent from FIG. 22, hemoglobin could be separated into five components, i.e. $A_{1a}$ (peak p22), $A_{1b}$ (peak p23), HbF (peak p24), $A_{1c}$ (peak p25) and $A_0$ (peak p26) in one cycle of 3.5 minutes under these measuring conditions. Peak p21 was the fast peak of a component having no interaction with the packing material. From the thus obtained chromatogram, retention time each of the individual components and theoretical plate number N of component $A_{1c}$ were obtained in the data processing section 24 which constituted a means for computing evaluation parameters. The results are shown in Table 4.

TABLE 4

| Sample No | Retention time (min.) | | | | | Theoretical plate number N | Pressure drop (kg/cm$^2$) |
|---|---|---|---|---|---|---|---|
| | $A_1a$ | $A_1b$ | HbF | $A_1c$ | A0 | | |
| 10 th | 0.50 | 0.80 | 1.70 | 2.20 | 2.70 | 1850 | 45 |
| | (100) | (100) | (100) | (100) | (100) | | |
| 1,300 th | 0.49 | 0.75 | 1.56 | 1.92 | 2.65 | 460 | 60 |
| | (98) | (94) | (88) | (87) | (98) | | |
| 1,300 th (Eluting condition changed) | 0.50 (100) | 0.78 (98) | 1.65 (97) | 2.10 (95) | 2.70 (100) | 730 | 60 |

Figures in parentheses show relative values to 10th sample, i.e. No. 10 sample, where the retention time each of the individual components was presumed to be 100.

As is apparent from Table 4, there was a tendency of smaller value of tr on 1,300th sample, as compared with 10th sample, where the tr value of component HbF was decreased by 88% and that of component $A_{1c}$ was decreased by 87%. Furthermore, the theoretical plate number N was decreased from 1,850 plates to 460 plates with broader peaks. That is, as shown in FIG. 23, separation of component $A_{1c}$ from HbF on the 1,300th sample was not satisfactory.

Figure 21:
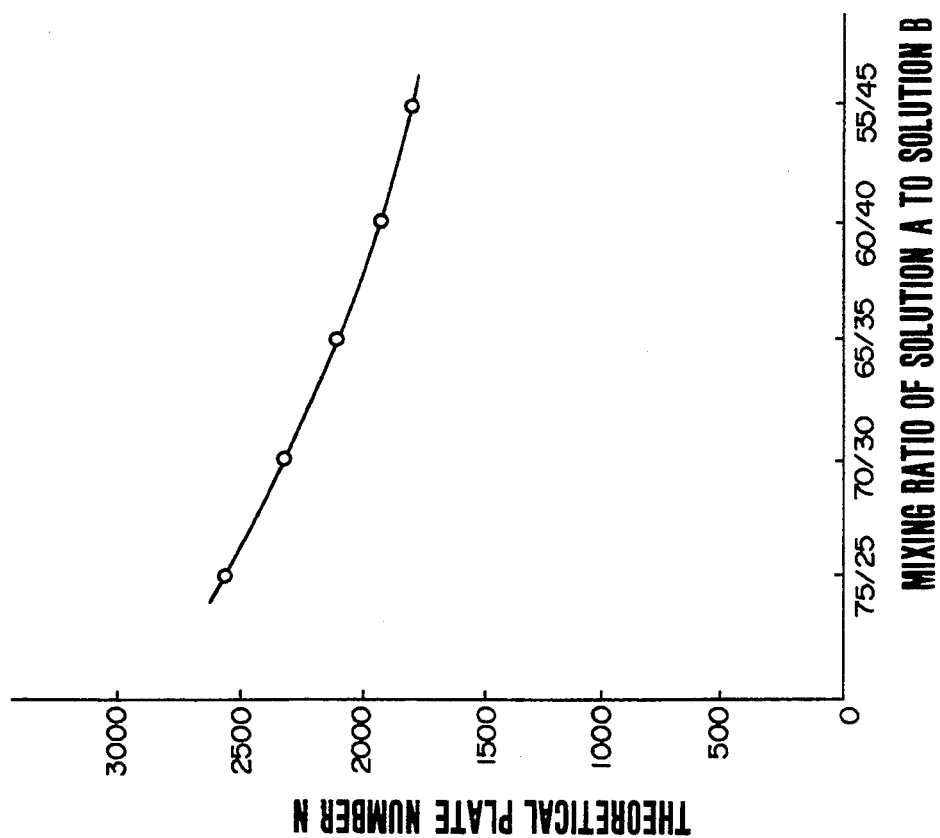
FIG. 21 is a diagram showing the mixing ratio of eluents and the theoretical plate number.
Figure 20:
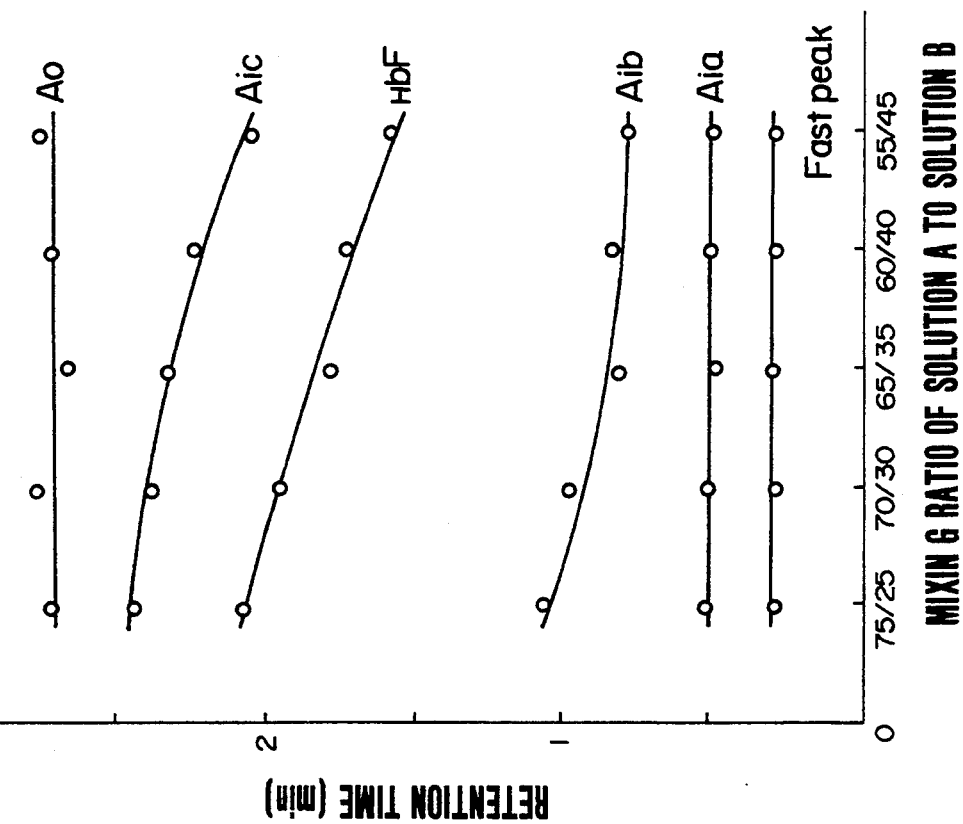
FIG. 20 is a diagram showing a relationship between the mixing ratio of eluents and the retention time.

On the other hand, FIGS. 20 and 21 show relationships of concentration of the first eluent, i.e. mixing ratio of solution A to solution B with retention time each of the individual Hb components and theoretical plate number N of component $A_{1c}$, respectively. These results are based on the above-mentioned stainless steel column 18 (4.6 mm in inner diameter and 35 mm in length) packed with the packing material (weakly acidic, cation exchange resin of methacrylate-based gel as a base material containing carboxymethyl groups as functional groups and having particle diameter of 4.1 m). Results shown in FIGS. 20 and 21 are based only on changing of mixing ratio of the first solution (i.e. mixing ratio of solution A to solution B) without changing the flow rate of eluent and switching time, and the column temperature initially set to 25° C. As is apparent from FIG. 20, there was such a tendency that tr values of components $A_{1b}$, HbF and $A_{1c}$ were increased with increasing ratio of solution A in the first solution, that is, with decreasing concentration of eluent. The tr values of components $A_{1a}$ and $A_0$ were almost constant even when the concentration of the first solution was changed.

As is also apparent from FIG. 21, there was such a tendency that the theoretical plate number N was increased with increasing ratio of solution A in the first solution, that is, with decreasing concentration of eluting solution, whereby peaks became sharp.

From relationships of concentration of the first solution, that is, mixing ratio of solution A to solution B, with tr values each of the individual componets and theoretical plate number N of component $A_{1c}$ in FIGS. 20 and 21, respectively, it is apparent that the chromatographic performance can be improved by increasing the ratio of solution A in the first solution, that is, by decreasing the concentration of the first solution in case the separation column performance is deteriorated (tr→smaller and N→smaller), as shown in FIG. 23.

In the foregoing separation column, good separation between components HbF and $A_{1c}$ and components $A_{1c}$ and $A_0$ could be obtained when the tr values of the individual Hb components were kept within ±10% and the theoretical plate number N was kept not less than 500 plates on the basis of the values on 10th sample.

Evaluation of separation column characteristics can be made by applying the foregoing experimental results of FIGS. 20 and 21 and the results of Table 5 to the flow chart of FIG. 19, and analysis can be carried out with high separation exactness by conducting control, etc. according to the separation column characteristics.

Figure 24:
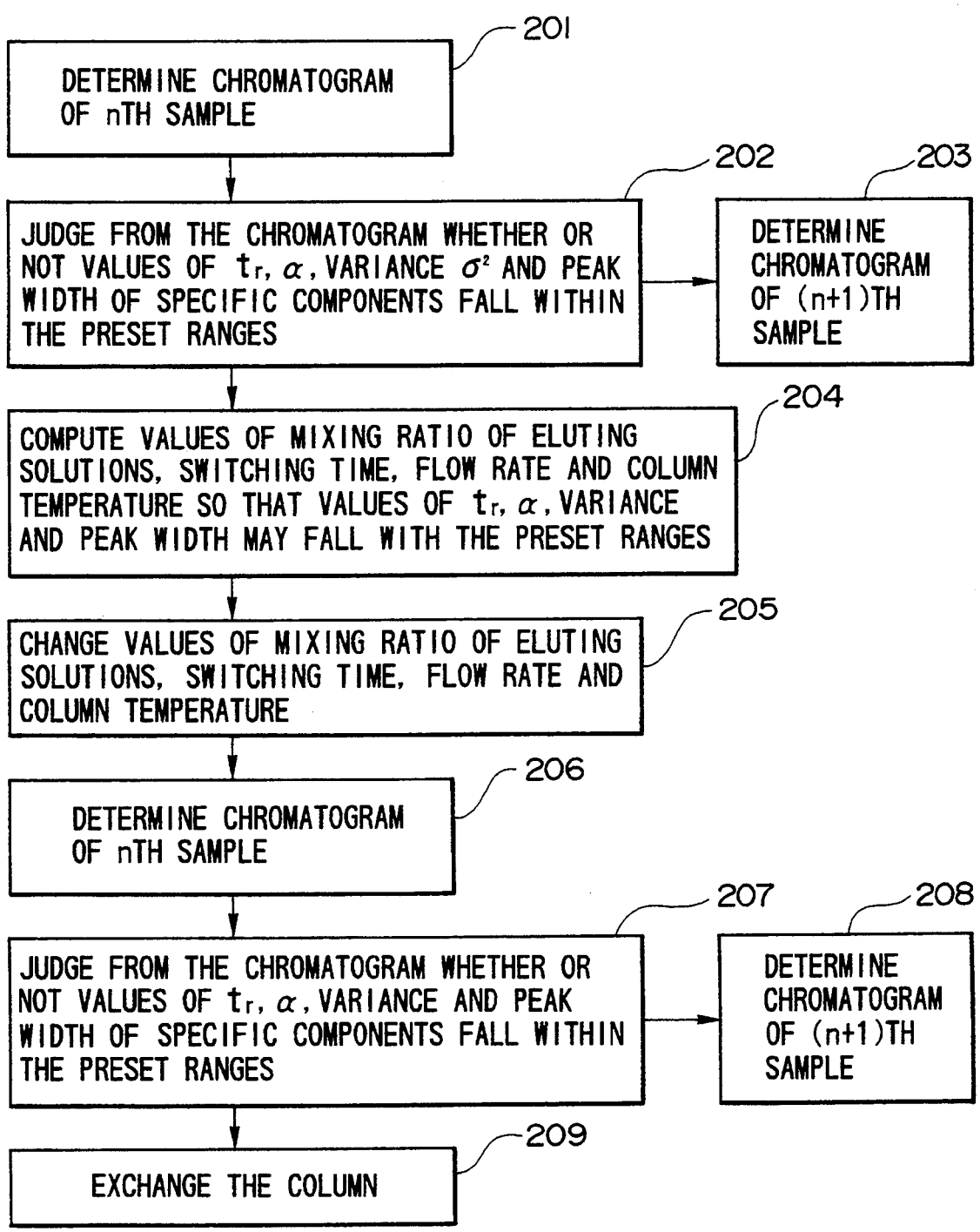
FIG. 24 is a flow chart for evaluation processing of another performances of separation column according to the present invention.

The foregoing explanation relates to a system for analysing glycated hemoglobin as one embodiment. When analysis is applied to a usual liquid chromatographic system, the flow chart will be that shown in FIG. 24, which is basically similar to that of FIG. 19. Thus, explanation of the flow chart of FIG. 24 will be omitted.

According to the present invention, a liquid chromatographic system capable of high speed analysis with high resolution can be provided with a packing material for analyzing vital body components in blood, i.e. hemoglobin, glycated hemoglobin or hemoglobin derivatives, protein, etc. with high speed and high separability, a separation column packed with the packing material to make the size of the column smaller, and eluents capable of assuring analyzing without any influence of changes in temperature.

5-component analysis or 6-component analysis can be conducted with high exactness in the present invention with a plurality of separation columns of different column lengths by using the same eluents, while adjusting flow rates of the eluents through the separation columns, etc.

In the present invention, life of separation column can be prolonged and high resolutioin and analyzing exactness can be prevented from lowering by judging deterioration of performance of separation column on the basis of measurement data of eluate from the separation column and changing the eluting conditions.

What is claimed is:

1. A liquid chromatographic system for separating and analyzing a stable type $A_{1c}$ component and an unstable type $A_{1c}$ component from hemoglobins in a blood sample and separating and analyzing $A_{1c}$ components from hemoglobins in a blood sample which comprises a means of sampling a sample and transferring the sample and at least one eluent to at least one separation column, a means of passing the eluent to the separation column, a means of detecting components separated in the separation column, and a means of computing a ratio of the detected components, wherein said separation column is packed with a porous methacrylic polymer having carboxylalkyl groups and a pore diameter of 600 to 1200 Å in a dry state, an ion exchange capacity of 0.1 to 0.5 meq/g on a dry basis, a pore volume of 0.2 to 0.6 ml/g in a dry state and a particle diameter of not more than 4 μm in a dry state.

2. A liquid chromatographic system according to claim 1, wherein the eluting conditions-indexing means conducts indexing of eluting conditions within a range that pressure drop of the separation column is kept within a range of preset values and the evaluation parameter is kept within the allowable range.

3. A liquid chromatographic system according to claim 1, wherein, when results of determining the chromatogram obtained under the changed eluting conditions by the evaluating means show deterioration of performance of the separation column, the evaluating means outputs a signal of at least one of the deterioration, of exchanging the separation columns, and of discontinuing sampling of samples.

4. A liquid chromatographic system according to claim 1, wherein the separation column comprises a first separation column for separating $A_{1c}$ component from hemoglobins in the blood sample and a second separation column for separating a stable $A_{1c}$ type component and an unstable type $A_{1c}$ component each from the hemoglobins in the blood sample, the first or second separation columns being subjected to continuous separation with one eluent or eluents having the same composition while cnanging a mixing ratio, a flow rate and a switching time of the eluent or eluents.

5. A liquid chromatographic system according to claim 4, wherein the first separation column is subjected to passage of the eluent or the eluents, thereby separating $A_{1c}$ components from hemoglobins in a blood sample, and obtaining a ratio of $A_{1c}$ components, and then the computing means determines whether or not the determined ratio of $A_{1c}$ components exceeds a preset value is judged, and when the determined ratio of $A_{1c}$ components exceeds the preset value, the sampling means samples the same blood sample as subjected to separation in the first separation column once again and transfers the blood sample to the second separation column, and the second separation column is subjected to passage of the eluent or eluents having the same composition as that for the first separation column, while changing at least one of the mixing ratio, the flow rate and the switching time of the eluent or the eluents, thereby separating the unstable type $A_{1c}$ component and the stable type $A_{1c}$ component.

6. A liquid chromatographic system according to claim 1, wherein an evaluation parameter-computing means for determining at least one of retention time, capacity factor, selection coefficient, full width or half width of peaks corresponding to individual components, standard deviation or variance of the peaks, ratio of peak width to peak height, asymmetrical factor of the peaks, theoretical plate number and linearity of base line as parameters for evaluating chromatographic performance of the separation column from detection data from the detecting means, an evaluating means for judging whether or not the determined evaluation parameters fall within the respective allowable ranges based on the respective predetermined standard values and determining deterioration of performance of the separation column, a data table for storing correlations predetermined between the evaluation parameters and eluting conditions for the separation column, an eluting condition-indexing means of indexing eluting conditions for allowing the evaluation parameters to fall within the respective allowable ranges, when the evaluation parameters judged by the evaluating means exceeds the respective allowable ranges, and an eluting condition-changing means of changing at least one of mixing ratio of the eluent, flow velocity or flow rate of the eluent, switching time of the eluent to be passed, and temperature of the separation column as eluting conditions on the basis of the indexed results are further provided.

7. A liquid chromatographic system according to claim 1 wherein the methacrylic polymer has a particle diameter of 3 to 4 μm in a dry state.

* * * * *